US012796715B2

(12) United States Patent
Drouillard et al.

(10) Patent No.: US 12,796,715 B2
(45) Date of Patent: Nov. 17, 2026

(54) ANIMAL FEED COMPOSITIONS AND METHODS OF USE

(71) Applicant: SYNGENTA CROP PROTECTION AG, Basel (CH)

(72) Inventors: James S. Drouillard, Olsburg, KS (US); Lucas Michael Horton, Manhattan, KS (US)

(73) Assignee: SYNGENTA CROP PROTECTION AG, Basel (CH)

( * ) Notice: Subject to any disclaimer, the term of this patent is extended or adjusted under 35 U.S.C. 154(b) by 94 days.

(21) Appl. No.: 18/047,414

(22) Filed: Oct. 18, 2022

(65) Prior Publication Data

US 2023/0270136 A1 Aug. 31, 2023

Related U.S. Application Data

(62) Division of application No. 16/603,621, filed as application No. PCT/US2018/030166 on Apr. 30, 2018, now abandoned.

(60) Provisional application No. 62/492,609, filed on May 1, 2017.

(51) Int. Cl.

| | |
|---|---|
| ***A23K 20/189*** | (2016.01) |
| ***A23K 10/30*** | (2016.01) |
| ***A23K 40/00*** | (2016.01) |
| ***A23K 50/10*** | (2016.01) |
| ***C12N 9/26*** | (2006.01) |
| ***C12N 9/30*** | (2006.01) |

(52) U.S. Cl.

CPC ............ *A23K 20/189* (2016.05); *A23K 10/30* (2016.05); *A23K 40/00* (2016.05); *A23K 50/10* (2016.05); *C12N 9/2414* (2013.01); *C12N 9/242* (2013.01); *C12Y 302/01001* (2013.01)

(58) Field of Classification Search

CPC ...... A23K 20/189; A23K 40/00; A23K 50/10; A23K 10/30; C12N 9/2414; C12N 9/242; C12Y 302/01001

See application file for complete search history.

(56) References Cited

U.S. PATENT DOCUMENTS

| | | | | |
|---|---|---|---|---|
| 5,543,576 | A | 8/1996 | van Ooijen et al. | |
| 5,714,474 | A | 2/1998 | Van Ooijen et al. | |
| 6,428,831 | B1 * | 8/2002 | Brown | A23K 40/20 426/511 |
| 6,586,028 | B1 | 7/2003 | Brown | |
| 6,723,370 | B2 | 4/2004 | Ulrich et al. | |
| 6,740,508 | B2 | 5/2004 | Ulrich | |
| 7,033,627 | B2 | 4/2006 | Van Ooyen et al. | |
| 7,102,057 | B2 | 9/2006 | Lanahan et al. | |
| 7,407,677 | B2 | 8/2008 | Callen et al. | |
| 7,557,262 | B2 | 7/2009 | Lanahan et al. | |
| 7,635,799 | B2 | 12/2009 | Johnson et al. | |
| 7,727,726 | B2 | 6/2010 | Cates | |
| 7,781,201 | B2 | 8/2010 | Callen et al. | |
| 7,785,855 | B2 | 8/2010 | Callen et al. | |
| 7,816,108 | B2 | 10/2010 | Callen et al. | |
| 7,855,322 | B2 | 12/2010 | Lanahan et al. | |
| 7,914,993 | B2 | 3/2011 | Batie et al. | |
| 7,915,020 | B2 | 3/2011 | Cates et al. | |
| 7,919,681 | B2 | 4/2011 | Lanahan et al. | |
| 8,003,863 | B1 | 8/2011 | Goodwin | |
| 8,093,453 | B2 * | 1/2012 | Johnson | C12N 9/2411 800/278 |
| 9,018,447 | B2 | 4/2015 | Lanahan et al. | |
| 9,125,357 | B2 | 9/2015 | Dallmier et al. | |
| 9,816,119 | B2 | 11/2017 | Aux | |
| 10,100,324 | B2 | 10/2018 | Ral et al. | |
| 10,196,669 | B2 | 2/2019 | Costello et al. | |
| 2003/0135885 | A1 | 7/2003 | Lanahan et al. | |
| 2005/0278803 | A1 | 12/2005 | Sewalt et al. | |
| 2005/0284380 | A1 | 12/2005 | Montgomery | |
| 2006/0230473 | A1 | 10/2006 | Johnson et al. | |
| 2007/0184175 | A1 | 8/2007 | Rubio et al. | |
| 2007/0243236 | A1 | 10/2007 | Cerda et al. | |
| 2009/0324571 | A1 | 12/2009 | Steinberg et al. | |
| 2010/0260918 | A1 | 10/2010 | Wang et al. | |
| 2014/0234279 | A1 | 8/2014 | Millan | |
| 2014/0234871 | A1 | 8/2014 | Dias | |
| 2015/0203860 | A1 | 7/2015 | Lanahan et al. | |
| 2017/0101663 | A1 | 4/2017 | Moser et al. | |

(Continued)

FOREIGN PATENT DOCUMENTS

| | | | |
|---|---|---|---|
| CN | 101342004 | A | 8/2008 |
| CN | 102363761 | A | 2/2012 |
| EP | 0449376 | B1 | 5/2001 |

(Continued)

OTHER PUBLICATIONS

ISAAA Inc, "Event Name: 3272", 2015, obtained Sep. 17, 2024 from http://web.archive.org/web/20150425213225/https://www.isaaa.org/gmapprovaldatabase/event/default.asp?EventID=111&Event=%7BrecEvents.EventName%7D (Year: 2015).*

(Continued)

*Primary Examiner* — Emily M Le
*Assistant Examiner* — James P. Shellhammer
(74) *Attorney, Agent, or Firm* — Karen A. Magri

(57) ABSTRACT

The invention provides an animal feed composition comprising plant material from a transgenic plant or plant part expressing a recombinant thermotolerant α-amylase. The invention further provides methods of improving feed utilization and decreasing liver abscesses. Also provided are methods of producing a steam flaked corn product, and the steam flaked corn product so produced.

6 Claims, 1 Drawing Sheet

Specification includes a Sequence Listing.

(56) References Cited

U.S. PATENT DOCUMENTS

2018/0030491 A1 2/2018 Aux

FOREIGN PATENT DOCUMENTS

| | | | |
|---|---|---|---|
| JP | S4969456 | A | 7/1974 |
| JP | 2016153406 | A2 | 3/2016 |
| RU | 2 073 715 | C1 | 2/1997 |
| RU | 2 533 001 | C2 | 11/2014 |
| UA | 10246 | | 12/1996 |
| WO | 2003000905 | A2 | 1/2003 |
| WO | 2003/018766 | A3 | 3/2003 |
| WO | 03/059087 | A1 | 7/2003 |
| WO | 2005096804 | A2 | 10/2005 |
| WO | 2006098952 | A2 | 9/2006 |
| WO | 2009/140504 | A1 | 11/2009 |
| WO | 2010088447 | A1 | 8/2010 |
| WO | 2010091221 | A1 | 8/2010 |
| WO | 2012004759 | A2 | 1/2012 |
| WO | 2016/164732 | A2 | 10/2016 |
| WO | 2017083196 | A1 | 5/2017 |
| WO | 2019/075028 | A1 | 4/2019 |

OTHER PUBLICATIONS

Zinn, R. A., et al. "Comparative effects of processing methods on the feeding value of maize in feedlot cattle." Nutrition Research Reviews 24.2 (2011): 183-190.
DD2008-70: Determination of the Safety of Syngenta Seeds Inc's Corn (*Zea mays* L. (Linnaeus)) Event 3272, Canadian Food Inspection Agency, Mar. 2008.
Determination of Nonregulated Status for Syngenta Seeds Event 3272 Corn (Alpha-amylase and phosphomannose isomerase corn), Animal and Plant Health Inspection Service, U.S. Department of Agriculture, Feb. 11, 2011.
National Environmental Policy Act Decision and Finding of No Significant Impact; Syngenta Seeds, Inc.; Alpha-Amylase Maize Event 3272; USDA, Aphis Biotechnology Regulatory Services dated Feb. 11, 2011.
Meale et al., "Board-Invited Review: Opportunities and challenges in using exogenous enzymes to improve ruminant production," Journal of Animal Science (2014), vol. 92: pp. 427-442.
"Application for import and use of genetically modified Event 3272 maize under Regulation (EC) No. 1829/2003", obtained from https://euginius.eu/euginius/api/literature/pdf/2170524150539240096, published 2013, 28 pages (2013).
"Novel Food Information", obtained from https://www.canada.ca/en/health-canada/services/food-nutrition/genetically-modified-foods-other-novel-foods/approved-products/alpha-amylase-corn-event-3272.html; published 2008 7 pages (2008).
"Scientific Opinion", EFSA J. 11:3252, 2013, 27 pages (2013).
Kung, L., "Silage Temperatures: How Hot is Too Hot?", Jul. 2011, 2 pages (2011).
Extended ESR for EP18794092.9, mailed on Jan. 14, 2021.
Qiao, Fu-Qiang et al.: "Effect of steam-flaking on chemical compositions, starch gelatinization, in vitro fermentability, and energetic values of maize, wheat and rice", Journal of Integrative Agriculture, vol. 14, No. 5, May 2015, pp. 949-955, XP055761304, Amsterdam, NL, ISSN: 2095-3119, DOI: 10.1016/S2095-3119(14)60913-8.
Hu, W. et al.: "Short communication: In vitro ruminal fermentability of a modified corn cultivar expressing a thermotolerant [alpha]-amylase", Journal of Dairy Science, vol. 93, No. 10, Oct. 2010, pp. 4846-4849, XP055761270, US, ISSN: 0022-0302, DOI: 10.3168/jds.2009-2321.
Mihalik, Daniel et al.: "Introduction of a synthetic Thermococcus-derived [alpha]-amiyase gene into barley genome for increased enzyme thermostability in grains", EJB Electronic Journal of Biotechnology, vol. 30, Nov. 2017, pp. 1-5, XP055761651, CL, ISSN: 0717-3458, DOI: 10.1016/j.ejbt.2017.08.002.
International Search Report dated Jul. 13, 2018 for International Patent Application No. PCT/US2018/030166.
International Search Report mailed Oct. 26, 2016 in Application No. PCT/US16/26656.
Supplementary European Search Report for EP16777361.3, mailed on Mar. 14, 2019.
Hu et al., "Short communication: In vitro ruminal fermentability of a modified corn cultivar expressing a thermotolerant a-amylase," J. Dairy Scl., 93:4846-4849 (2010).
Schoonmaker et al., "Effect of feeding corn modified to contain a unique amylase on performance and carcass characteristics of feedlot steers," The Professional Animal Scientist 30 (2014) 561-565.
Response to APHIS/BRS Review for Technical Completeness of Syngenta's petition for a Determination of Non-regulated Status for Corn Event 3272, assigned APHIS No. 05-280-01p (Jan. 10, 2007).
Robert Plamondon, "Save money on chicken feed," Mother Earth News (Jul. 29, 2019).
Leahy et al., "Effects of treating corn silage with alpha-amylase and (or) sorbic acid on beef cattle growth and carcass characteristics," J. Anim. Sci. (1990), 68: pp. 490-497.
Miller et al., "Effect of altering the physical form of corn silage on utilization by dairy cattle," Journal of Dairy Science, vol. 52, No. 12, pp. 1955-1960.
Syngenta Seeds, Inc. Alpha-Amylase Maize Event 3272, OECD Unique Identifier SYN-E3272-5, Final Environmental Assessment, Feb. 2011, USDA APHIS.
Tricarico et al., "Effects of a dietary Aspergillus oryzae extract containing-amylase activity on performance and carcass characteristics of finishing beef cattle," Journal of Animal Science (Mar. 2007) published online Nov. 22, 2006 @ https://www.researchgate.net/publication/6676016; pp. 1-34.
Nagaraja and Chengappa, "Liver Abscesses in Feedlot Cattle: A Review" American Society of Animal Science, (1998), 76:287-298.
International Preliminary Report on Patentability for International Application No. PCT/US2018/030166, mailed Nov. 14, 2019, 8 Pages.
Iragavarapu et al., BDH58985, SEQ ID No. 1, Dec. 1, 2016, 2 Pages.
Myat I., et al., "Effect of Thermostable-Amylase Injection on Mechanical and Physiochemical Properties for Saccharification of Extruded Corn Starch," Journal of the Science of Food and Agriculture, Jul. 8, 2013, vol. 94, No. 2, pp. 288-295.

* cited by examiner

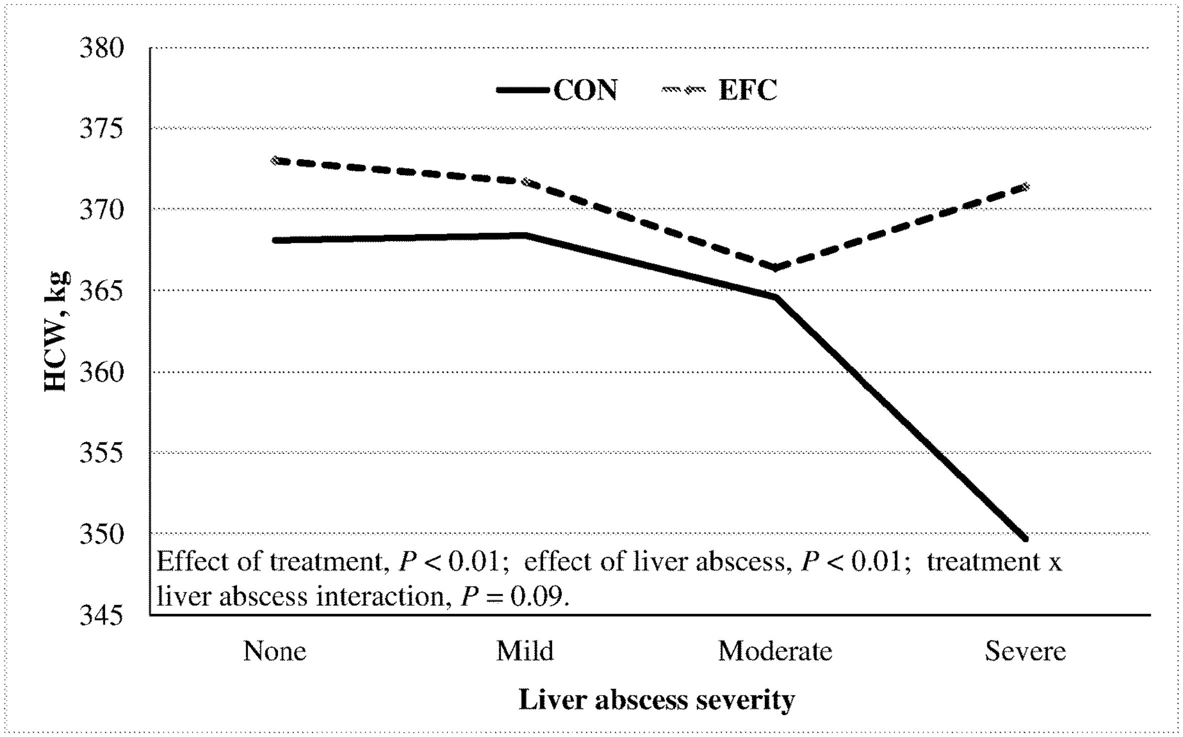
380
375
370
365
360
355
350
345
CON
EFC
HCW, kg
Effect of treatment, P < 0.01; effect of liver abscess, P < 0.01; treatment x liver abscess interaction, P = 0.09.
None
Mild
Moderate
Severe
Liver abscess severity

ANIMAL FEED COMPOSITIONS AND METHODS OF USE

RELATED APPLICATION INFORMATION

This application is a divisional of U.S. application Ser. No. 16/603,621 (pending), which claims priority under 35 U.S.C. § 371 from International Application No. PCT/US2018/030166, filed 30 Apr. 2018, which claims the benefit of U.S. provisional patent application Ser. No. 62/492,609, filed 1 May 2017, the disclosures of said applications are incorporated by reference herein in their entirety.

STATEMENT REGARDING ELECTRONIC SUBMISSION OF A SEQUENCE LISTING

A Sequence Listing in ST26 compliant format, entitled "Animal Feed Compositions and Methods of Use.xml", 15.0 KB (15,425 bytes) in size, generated on Oct. 17, 2022 and filed via EFS-WEB is provided in lieu of a paper copy. This Sequence Listing is hereby incorporated by reference into the specification for its disclosures.

FIELD OF THE INVENTION

The present invention relates to animal feed compositions and methods of making and using the same.

BACKGROUND OF THE INVENTION

Animal feeds can be classified into two groups: (1) concentrates or compound feeds and (2) roughages. Concentrates or compound feeds are high in energy value, including fat, cereal grains and their by-products (barley, corn, oats, rye, wheat), high-protein oil meals or cakes (soybean, canola, cottonseed, peanut and the like), and by-products from processing of sugar beets, sugarcane, animals, and fish, which can be produced in the form of pellets or crumbles. Concentrates or compound feeds can be complete in that they can provide all the daily required food needs or they can provide a part of the ration, supplementing whatever else may be provided as a food ration. Roughage includes pasture grasses, hays, silage, root crops, straw, and stover (cornstalks).

Feed constitutes the largest cost of raising animals for food production. Thus, the present invention is directed to compositions and methods for improving the efficiency of animal feed utilization, thereby reducing the cost of production.

In addition, in feedlot cattle, liver abscesses caused by pyogenic bacteria are common. The prevalence of liver abscesses increases with low forage/high concentrate diets. Reduction of liver abscesses in feedlot cattle results in improved live weight, carcass weight, dressing percentage and carcass trim. Cattle with severe liver abscesses may require additional carcass trimming and in some instances, condemnation of entire viscera. Rupture of an abscess can lead to carcass contamination resulting in interrupted carcass flow, lost time, increased costs and increased labor.

SUMMARY OF THE INVENTION

One aspect of the present invention provides an animal feed composition comprising microbial α-amylase and methods of using the animal feed composition to decrease liver abscesses in cattle. In some aspects, the microbial α-amylase comprises a polypeptide having at least about 80% identity to the amino acid sequence of SEQ ID NO:1 or a polypeptide encoded by a nucleotide sequence having at least about 80% identity to the nucleotide sequence of SEQ ID NO:2, SEQ ID NO:3, SEQ ID NO:4 and/or SEQ ID NO:5. In some aspects the animal feed composition comprises steam-flaked corn expressing a microbial α-amylase. Also provided are methods of producing a steam flaked corn product by steam flaking corn kernels from a transgenic corn plant expressing a microbial α-amylase, and the steam flaked corn product produced thereby.

BRIEF DESCRIPTION OF THE DRAWINGS

FIG. 1 shows the relationship between liver abscess severity and HCW for each treatment.

DETAILED DESCRIPTION OF THE INVENTION

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage, an amount or a time period and the like, is meant to encompass variations of ±20%, ±10%, ±5%, ±1%, ±0.5%, or even ±0.1% of the specified amount (e.g., an amount of weight gained or feed provided).

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The present invention is directed to compositions and methods for improving the efficiency of animal feed utilization, thereby reducing the cost of production. The present inventors have made the surprising discovery that animals fed an animal feed composition comprising microbial α-amylase can have an increase in the average daily weight gain or growth rate, an increase in the efficiency of feed utilization or require a reduced number of days to achieve a desired weight as compared to animals not fed said feed composition.

Accordingly, in one aspect of the invention, an animal feed composition comprising microbial α-amylase is provided. In further aspects of the invention, the microbial α-amylase comprises a polypeptide having at least 80% identity to the amino acid sequence of SEQ ID NO:1 or a polypeptide encoded by a nucleotide sequence having at least 80% identity to the nucleotide sequence of SEQ ID NO:2, SEQ ID NO:3, SEQ ID NO:4 and/or SEQ ID NO:5. In some embodiments, the α-amylase is a liquid. Thus, in some embodiments of the invention, an animal feed composition of the invention can be a supplement that comprises a liquid microbial α-amylase that can be added to the feed provided to an animal.

In another aspect, the present invention provides an animal feed composition comprising plant material, wherein the plant material comprises an expressed recombinant α-amylase. In some particular embodiments, the expressed recombinant α-amylase is encoded by a nucleotide sequence having at least about 80% identity to the nucleotide sequence of SEQ ID NO:2, SEQ ID NO:3, SEQ ID NO:4 and/or SEQ ID NO:5 or comprises a polypeptide having at least about 80% identity to the amino acid sequence of SEQ ID NO:1. Thus, in further embodiments, the invention provides an animal feed composition comprising plant material from a transgenic plant or plant part comprising a recombinant α-amylase encoded by a nucleotide sequence having at least about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1.

In particular embodiments, the transgenic plant or plant part can comprise about 1% to about 100% by weight of the plant material. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, or any range therein. Thus, in some embodiments, the plant material can comprise one or more different types of plants. Thus, for example, the plant material can be from a plant in which recombinant or heterologous (e.g., microbial) α-amylase is expressed. In other embodiments, the plant material comprises, consists essentially of, or consists of material from a plant in which recombinant or heterologous (e.g., microbial) α-amylase is expressed and material from a plant not expressing said recombinant or heterologous α-amylase (e.g., a commodity plant). Thus, in some embodiments, when the plant material comprises material from a plant in which recombinant or heterologous (e.g., microbial) α-amylase is expressed and material from a plant not expressing said recombinant or heterologous α-amylase (e.g., a commodity plant), the material from a plant in which recombinant or heterologous (e.g., microbial) α-amylase is expressed can comprise from about 1% to about 99% by weight of the plant material and the material from a plant not expressing said recombinant or heterologous α-amylase can comprise from about 99% to about 1% by weight of the plant material.

In further embodiments, plant material can comprise from about 5% to about 100% by weight of the animal feed composition. Thus, for example, the plant material can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein.

The animal feed of the invention can be in any form that is useful with this invention. Thus, in some embodiments, the form of the animal feed can be, but is not limited to, pellets, grain including one or more types of grain mixed (i.e., mixed grain), a mixture of grain and pellets, silage, dry-rolled, steam flaked, whole kernel, coarsely cracked kernels (e.g., coarsely cracked corn), high moisture corn and/or any combination thereof. In some embodiments, the animal feed can comprise other components, including but not limited to coarsely cracked kernels, wet distillers grain, dry distillers grain, corn silage, supplements/liquid supplements, corn gluten feed, and/or ground hay.

As used herein, the term "plant material" includes any plant part, including but not limited to endosperm, embryos (germ), pericarp (bran coat), pedicle (tip cap), pollen, ovules, seeds (grain), leaves, flowers, branches, stems, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the invention can be in the form of an isolated single cell or can be a cultured cell or can be a part of a higher-organized unit such as, for example, a plant tissue or a plant organ. A "protoplast" is an isolated plant cell without a cell wall or with only parts of the cell wall. Thus, in some embodiments of the invention, a transgenic plant or plant part comprising a recombinant α-amylase encoded by a nucleotide sequence of the invention comprises a cell comprising said recombinant α-amylase encoded by a nucleotide sequence of the invention, wherein the cell is a cell of any plant or plant part including, but not limited to, a root cell, a leaf cell, a tissue culture cell, a seed cell, a flower cell, a fruit cell, a pollen cell, and the like. In representative embodiments, the plant material can be a seed or grain.

The plant material can be from any plant. In some embodiments, the plant material is from a plant in which recombinant or heterologous (e.g., microbial) α-amylase can be expressed. Further, as discussed herein, in other embodiments, the plant material can be a mixture of plant material from a plant in which recombinant or heterologous (e.g., microbial) α-amylase is expressed and from a plant not expressing said recombinant or heterologous α-amylase (e.g., a commodity plant). Thus, in representative embodiments, the plant material can be a mixture of normal "commodity" plant material (e.g., commodity corn) and plant material from a transgenic plant of the present invention expressing recombinant or heterologous α-amylase.

Thus, in some embodiments, the plant material can be from a corn plant, a sorghum plant, a wheat plant, a barley plant, a rye plant, an oat plant, a rice plant, and/or a millet plant. In representative embodiments, the plant material can be from a corn plant. In other embodiments, the plant material can be a seed or grain from a corn plant. In particular embodiments, the plant material can be a corn plant comprising corn event 3272 (see, U.S. Pat. No. 8,093,453).

In some embodiments, the invention provides a "total mixed ration" comprising plant material from a transgenic corn plant or plant part stably transformed with a recombinant α-amylase encoded by a nucleotide sequence having about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1. As used herein, "total mixed ration" can mean the 24 hour feed allowance for an individual animal that includes, for example, plant material from a transgenic corn plant or plant part (e.g., corn kernels, coarsely cracked corn, and the like), supplements and additives, (e.g., vitamins and minerals), and/or "roughages" (e.g., pasture grasses, hays, silage, root crops, straw, and stover (cornstalks)).

In some embodiments, the plant material from the transgenic corn plant or plant part comprises from about 1% to about 100% by weight of the total mixed ration. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, and/or any range therein.

In other embodiments, an animal feed composition is provided that comprises a total mixed ration of the invention. In some embodiments, the total mixed ration can comprise about 5% to about 100% by weight of the animal feed composition. Thus, for example, the total mixed ration can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein. In representative embodiments, the total mixed ration comprises about 50% of the animal feed composition.

In still further embodiments, the invention provides a corn ration comprising plant material from a transgenic corn plant or plant part stably transformed with a recombinant α-amylase encoded by a nucleotide sequence having about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1. As used herein, "corn ration" means the 24 hour corn allowance for an individual animal.

In some embodiments, the plant material from the transgenic corn plant or plant part comprises from about 1% to about 100% by weight of the corn ration. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, and/or any range therein.

In other embodiments, an animal feed composition is provided that comprises a corn ration of the invention. In some embodiments, the corn ration can comprise about 5% to about 100% by weight of the animal feed composition. Thus, for example, the corn ration can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein. In representative embodiments, the corn ration comprises about 50% of the animal feed composition.

In some embodiments, the total mixed ration can comprise wet corn gluten feed that can be about 10% to about 40% by weight of the animal feed composition. In further embodiments the total mixed ration can comprise wet corn gluten feed that can be about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, by weight of the animal feed composition.

In other embodiments, the total mixed ration can comprise modified distillers grains with solubles that can be about 5% to about 25% by weight of the animal feed composition. In further embodiments the total mixed ration can comprise modified distillers grains with solubles that can be about 5%, 6%, 7%, 8%, 9%, 10%, 11%, 12%, 13%, 14%, 15%, 16%, 17%, 18%, 19%, 20%, 21%, 22%, 23%, 24%, 25%, by weight of the animal feed composition.

In other embodiments, the total mixed ration can comprise modified distillers grains with solubles that can be about 5% to about 25% by weight of the animal feed composition. In further embodiments the total mixed ration can comprise dry distillers grains that can be about 5%, 6%, 7%, 8%, 9%, 10%, 11%, 12%, 13%, 14%, 15%, 16%, 17%, 18%, 19%, 20%, 21%, 22%, 23%, 24%, 25%, by weight of the animal feed composition.

In further embodiments, the total mixed ration can comprise wet distillers grains with solubles that can be about 5% to about 25% by weight of the animal feed composition. In further embodiments the total mixed ration can comprise wet distillers grains with solubles that can be about 5%, 6%, 7%, 8%, 9%, 10%, 11%, 12%, 13%, 14%, 15%, 16%, 17%, 18%, 19%, 20%, 21%, 22%, 23%, 24%, 25%, by weight of the animal feed composition.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention (e.g., SEQ ID NO:1, SEQ ID NO:2, SEQ ID NO:3, SEQ ID NO:4, SEQ ID NO:5). "Orthologous," as used herein, refers to homologous nucleotide sequences and/or amino acid sequences in different species that arose from a common ancestral gene during speciation. A homologue of this invention has a significant sequence identity (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO:1, SEQ ID NO:2, SEQ ID NO:3, SEQ ID NO:4 or SEQ ID NO:5.

A homologue of SEQ ID NO:1, SEQ ID NO:2, SEQ ID NO:3, SEQ ID NO:4 and/or SEQ ID NO:5 can be utilized with any feed composition or method of the invention, alone or in combination with one another and/or with SEQ ID NO:1, SEQ ID NO:2, SEQ ID NO:3, SEQ ID NO:4 and/or SEQ ID NO:5.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The phrase "substantially identical," in the context of two nucleic acid molecules, nucleotide sequences or protein sequences, refers to two or more sequences or subsequences that have at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms, described herein and as known in the art, or by visual inspection. In some embodiments of the invention, the substantial identity exists over a region of the sequences that is at least about 50 residues to about 200 residues, about 50 residues to about 150 residues, and the like, in length. Thus, in some embodiments of the invention, the substantial identity exists over a region of the sequences that is at least about 50, about 60, about 70, about 80, about 90, about 100, about 110, about 120, about 130, about 140, about 150, about 160, about 170, about 180, about 190, about 200, or more residues in length. In a further embodiment, the sequences are substantially identical over the entire length of the coding regions. Furthermore, in representative embodiments, substantially identical nucleotide or protein sequences perform substantially the same function (e.g., α-amylase activity). Thus, in some particular embodiments, the sequences are substantially identical over at least about 150 residues and have α-amylase activity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990. *J. Mol. Biol.* 215: 403). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5 °C lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or Northern blot is 50% formamide with 1 mg of heparin at 42 °C, with the hybridization being carried out overnight. An example of highly stringent wash conditions is 0.15M NaCl at 72 °C for about 15 minutes. An example of stringent wash conditions is a 0.2×SSC wash at 65 °C for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45 °C for 15 minutes. An example of a low stringency wash for a duplex of, e.g., more than 100 nucleotides, is 4-6×SSC at 40 °C for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30 °C. Stringent conditions can also be achieved with the addition of destabilizing agents such as formamide. In general, a signal to noise ratio of 2λ or higher than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences (e.g., SEQ ID NO:2, SEQ ID NO:3, SEQ ID NO:4, SEQ ID NO:5). In one embodiment, a reference nucleotide sequence hybridizes to the "test" nucleotide sequence in 7% sodium dodecyl sulfate (SDS), 0.5 M $NaPO_4$, 1 mM EDTA at 50 °C with washing in 2×SSC, 0.1% SDS at 50 °C. In another embodiment, the reference nucleotide sequence hybridizes to the "test" nucleotide sequence in 7% sodium dodecyl sulfate (SDS), 0.5 M $NaPO_4$, 1 mM EDTA at 50 °C with washing in 1×SSC, 0.1% SDS at 50 °C or in 7% sodium dodecyl sulfate (SDS), 0.5 M $NaPO_4$, 1 mM EDTA at 50 °C with washing in 0.5×SSC, 0.1% SDS at 50 °C. In still further embodiments, the reference nucleotide sequence hybridizes to the "test" nucleotide sequence in 7% sodium dodecyl sulfate (SDS), 0.5 M $NaPO_4$, 1 mM EDTA at 50 °C with washing in 0.1×SSC, 0.1% SDS at 50 °C, or in 7% sodium dodecyl sulfate (SDS), 0.5 M $NaPO_4$, 1 mM EDTA at 50 °C with washing in 0.1×SSC, 0.1% SDS at 65 °C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

Accordingly, in some embodiments of the invention, nucleotide sequences having significant sequence identity to the nucleotide sequence of SEQ ID NO:2, SEQ ID NO:3, SEQ ID NO:4 and/or SEQ ID NO:5 are provided. "Significant sequence identity" or "significant sequence similarity" means at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identity or similarity with another nucleotide sequence. Thus, in additional embodiments, "significant sequence identity" or "significant sequence similarity" means a range of about 70% to about 100%, about 75% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, and/or about 99% to about 100% identity or similarity with another nucleotide sequence. Therefore, in some embodiments, a nucleotide sequence of the invention is a nucleotide sequence that has significant sequence identity to the nucleotide sequence of SEQ ID NO:2, SEQ ID NO:3, SEQ ID NO:4 or SEQ ID NO:5 and encodes a polypeptide having α-amylase activity. In some embodiments, a nucleotide sequence of the invention is a nucleotide sequence that has 80% to 100% identity to the nucleotide sequence of SEQ ID NO:2, SEQ ID NO:3, SEQ ID NO:4 or SEQ ID NO:5 and encodes a polypeptide having α-amylase activity. In representative embodiments, a nucleotide sequence of the invention is a nucleotide sequence that has 95% identity to the nucleotide sequence of SEQ ID NO:2, SEQ ID NO:3, SEQ ID NO:4 or SEQ ID NO:5 and encodes a polypeptide having α-amylase activity.

In some embodiments, a polypeptide of the invention comprises, consists essentially of, or consists of an amino acid sequence that is at least 70% identical, e.g., at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identical to the amino acid sequence of SEQ ID NO:1 and has α amylase activity.

In some embodiments, a polypeptide or nucleotide sequence can be a conservatively modified variant. As used herein, "conservatively modified variant" refer to polypeptide and nucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., α-amylase activity) as described herein. The variant can result from, for example, a genetic polymorphism or human manipulation. A biologically active variant of the reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity or similarity (e.g., about 40% to about 99% or more sequence identity or similarity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

For example, amino acid sequence variants of the reference polypeptide can be prepared by mutating the nucleotide sequence encoding the enzyme. The resulting mutants can be expressed recombinantly in plants, and screened for those that retain biological activity by assaying for α-amylase activity using methods well known in the art. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and Techniques in *Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complimentary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.), herein incorporated by reference.

The deletions, insertions and substitutions in the polypeptides described herein are not expected to produce radical changes in the characteristics of the polypeptide (e.g., the activity of the polypeptide). However, when it is difficult to predict the exact effect of the substitution, deletion or insertion in advance of doing so, one of skill in the art will appreciate that the effect can be evaluated by routine screening assays that can screen for the particular polypeptide activities of interest (e.g., α-amylase activity).

In some embodiments, the compositions of the invention can comprise active fragments of the polypeptide. As used herein, "fragment" means a portion of the reference polypeptide that retains the polypeptide activity of α-amylase. A fragment also means a portion of a nucleic acid molecule encoding the reference polypeptide. An active fragment of the polypeptide can be prepared, for example, by isolating a portion of a polypeptide-encoding nucleic acid molecule that expresses the encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, or 2200 contiguous nucleotides, or any range therein, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, 500, 525, 550, 525, 550, 600, 625, 650, 675, or 700 contiguous amino acid residues, or any range therein, or up to the total number of amino acid residues present in the full-length polypeptide. Thus, in some embodiments, the invention provides a polypeptide comprising, consisting essentially of, or consisting of at least about 150 contiguous amino acid residues of a polypeptide of the invention (e.g., SEQ ID NO:1) and having α-amylase activity.

As used herein, the terms "express," "expresses," "expressed" or "expression," and the like, with respect to a nucleic acid molecule and/or a nucleotide sequence (e.g., RNA or DNA) indicates that the nucleic acid molecule and/or nucleotide sequence is transcribed and, optionally, translated. Thus, a nucleic acid molecule and/or nucleotide sequence may express or produce a polypeptide of interest or a functional untranslated RNA.

A "heterologous" or "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or nucleic acid molecules of the invention can be operatively associated with a variety of promoters for expression in host cells (e.g., plant cells). As used herein, "operatively associated with," when referring to a first nucleic acid sequence that is operatively linked to a second nucleic acid sequence, means a situation when the first nucleic acid sequence is placed in a functional relationship with the second nucleic acid sequence. For instance, a promoter is operatively associated with a coding sequence if the promoter effects the transcription or expression of the coding sequence.

A DNA "promoter" is an untranslated DNA sequence upstream of a coding region that contains the binding site for RNA polymerase and initiates transcription of the DNA. A "promoter region" can also include other elements that act as regulators of gene expression. Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes. In particular aspects, a "promoter" useful with the invention is a promoter capable of initiating transcription of a nucleotide sequence in a cell of a plant.

A "chimeric gene" is a recombinant nucleic acid molecule in which a promoter or other regulatory nucleotide sequence is operatively associated with a nucleotide sequence that codes for an mRNA or which is expressed as a protein, such that the regulatory nucleotide sequence is able to regulate transcription or expression of the associated nucleotide sequence. The regulatory nucleotide sequence of the chimeric gene is not normally operatively linked to the associated nucleotide sequence as found in nature.

The choice of promoter will vary depending on the temporal and spatial requirements for expression, and also depending on the host cell to be transformed. Thus, for example, expression of a nucleotide sequence can be in any plant and/or plant part, (e.g., in leaves, in stalks or stems, in ears, in inflorescences (e.g., spikes, panicles, cobs, etc.), in roots, seeds and/or seedlings, and the like). Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. Further, the promoter expression cassettes described by McElroy et al. (*Mol. Gen. Genet.* 231: 150-160 (1991)) can be easily modified for the expression of nucleotide sequences and are particularly suitable for use in monocotyledonous hosts.

In some embodiments, tissue specific/tissue preferred promoters can be used. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein (e.g., gamma zein) or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of nucleotide sequences in plants, particularly maize, include but are not limited to those that direct expression in root, pith, leaf or pollen. Such promoters are disclosed, for example, in PCT Publication WO 93/07278, herein incorporated by reference in its entirety. Other non-limiting examples of tissue specific or tissue preferred promoters include the cotton rubisco promoter disclosed in U.S. Pat. No. 6,040,504; the rice sucrose synthase promoter disclosed in U.S. Pat. No. 5,604,121; the root specific promoter described by de Framond (*FEBS* 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in PCT Publication WO 01/73087, all incorporated by reference herein.

Additional examples of tissue-specific/tissue preferred promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: Genetic Engineering of Plants (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. In some embodiments, the promoter can be an endosperm-specific promoter including but not limited to a maize gamma-zein promoter or a maize ADP-gpp promoter.

Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) Annu. *Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

A polypeptide of this invention may or may not be targeted to a compartment within the plant through use of a signal sequence. Numerous signal sequences are known to influence the expression or targeting of a polynucleotide to a particular compartment/tissue or outside a particular compartment/tissue. Suitable signal sequences and targeting promoters are known in the art and include, but are not limited to, those provided herein (see, e.g., U.S. Pat. No. 7,919,681). Examples of targets include, but are not limited to, the vacuole, endoplasmic reticulum (ER), chloroplast, amyloplast, starch granule, cell wall, seed, or to a particular tissue, e.g., endosperm. Thus, a nucleotide sequence encoding a polypeptide of the invention (e.g., SEQ ID NO:1) can be operably linked to a signal sequence for targeting and/or retaining the polypeptide to a compartment within a plant. In some embodiments, the signal sequence may be an N-terminal signal sequence from waxy, an N-terminal signal sequence from gamma-zein, a starch binding domain, or a C-terminal starch binding domain. In further embodiments, the signal sequence can be an ER signal sequence, an ER retention sequence, an ER signal sequence and an additional ER retention sequence. Thus, in some embodiments of the invention, the α-amylase polypeptides can be fused with one or more signal sequences (and/or nucleotide sequences encoding said polypeptides can be operably linked to nucleotide sequences encoding said signal sequences).

As used herein, "expression cassette" means a nucleic acid molecule comprising a nucleotide sequence of interest (e.g., the nucleotide sequence of SEQ ID NO:2, SEQ ID NO:3, SEQ ID NO:4 and/or SEQ ID NO:5), wherein said nucleotide sequence is operatively associated with at least a control sequence (e.g., a promoter). Thus, some embodiments of the invention provide expression cassettes designed to express the nucleotide sequence of SEQ ID NO:2, SEQ ID NO:3, SEQ ID NO:4 and/or SEQ ID NO:5. In this manner, for example, one or more plant promoters operatively associated with the nucleotide sequence of SEQ ID NO:2, SEQ ID NO:3, SEQ ID NO:4 and/or SEQ ID NO:5 or a nucleotide sequence having substantial identity to the nucleotide sequence of SEQ ID NO:2, SEQ ID NO:3, SEQ ID NO:4 and/or SEQ ID NO:5 can be provided in an expression cassette for expression in an organism or cell thereof (e.g., a plant, plant part and/or plant cell).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to a nucleotide sequence to be expressed, an expression cassette can also include other regulatory sequences. As used herein, a "regulatory sequence" means a nucleotide sequence located upstream (5' non-coding sequences), within and/or downstream (3' non-coding sequences) of a coding sequence, and/or which influences the transcription, RNA processing or stability, or translation of the associated coding sequence. Regulatory sequences include, but are not limited to, promoters, enhancers, introns, translation leader sequences, termination signals, and polyadenylation signal sequences. In some embodiments, an expression cassette can also include nucleotide sequences encoding signal sequences operably linked to a polynucleotide sequence of the invention.

For purposes of the invention, the regulatory sequences or regions can be native/analogous to the plant, plant part and/or plant cell and/or the regulatory sequences can be native/analogous to the other regulatory sequences. Alternatively, the regulatory sequences may be heterologous to the plant (and/or plant part and/or plant cell) and/or to each other (i.e., the regulatory sequences). Thus, for example, a promoter can be heterologous when it is operatively linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and/or polynucleotide) are substantially modified from their original form and/or genomic locus, and/or the promoter is not the native promoter for the operably linked polynucleotide.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' noncoding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tm1 terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella* ozaenae that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

In other aspects of the invention a method of increasing the growth rate (weight gain) or the average daily weight gain of an animal is provided, the method comprising feeding to said animal an animal feed composition of the present invention, wherein the growth rate of the animal or the average daily weight gain of the animal is increased by about 0.05 lb/day to about 10 lbs/day as compared to the growth rate of a control animal that is not provided the animal feed composition of the invention. Thus, in some embodiments the increase in growth rate or average daily weight gain can be about 0.05, 0.06, 0.07, 0.08, 0.09, 0.1, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.25, 1.5, 1.75, 2, 2.25, 2.5, 2.75, 3, 3.25, 3.5, 3.75, 4, 4.1, 4.2, 4.21, 4.22, 4.23, 4.24, 4.25, 4.26, 4.27, 4.28, 4.29, 4.3, 4.31, 4.32, 4.33, 4.34, 4.35, 4.36, 4.37, 4.38, 4.39, 4.4, 4.41, 4.42, 4.43, 4.44, 4.45, 4.46, 4.47, 4.48, 4.49, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10 lbs/day, and the like and/or any range therein. In some particular embodiments, the increase in growth rate or average daily weight gain can be from about 0.05 lb/day to about 0.5 lb/per day. In further embodiments, the increase in growth rate or average daily weight gain can be about 0.1 lb/day as compared to the growth of a control animal that is not provided said animal feed composition.

In still further aspects of the invention, a method for reducing the number of days needed to achieve a desired weight in an animal is provided, the method comprising feeding to said animal an animal feed composition of the invention, thereby reducing the number of days needed to achieve a desired weight as compared to the number of days needed to achieve the same desired weight in a control animal that is not fed said animal feed composition.

As used herein, a "desired weight" "or desired finished weight" can mean a live weight or a hot carcass weight. Thus, for example, for cattle, a desired live weight can be between about 950 to about 1,600 lbs and a desired hot carcass weight can be between about 700 to about 1,000 lbs.

Prior to entering a feedlot, cattle spend most of their life grazing on range or pasture land and then are transported to a feedlot for finishing where they are fed grain and other feed concentrates. Generally, cattle enter a feedlot at a weight of about 600 to about 750 lbs. Depending on weight at placement, the feeding conditions, and the desired finished weight, the period in a feedlot can be in a range from about 90 days to about 300 days. The average gain can be from about 2.5 to about 5 pounds per day.

Accordingly, in another aspect of the invention, the number of days needed to achieve a desired weight in an animal fed the animal feed compositions of the invention can be reduced by about 1 day to about 30 days as compared to a control animal that is not fed said animal feed composition. In some embodiments, the number of days needed to achieve a desired weight in an animal fed the animal feed compositions of the invention can be reduced by about 1 day to about 25 days, about 1 day to about 20 days, about 5 days to about 20 days, about 5 days to about 15 days, and the like, as compared to a control animal that is not fed said animal feed composition. Thus, in some embodiments, the number of days needed to achieve a desired weight in an animal fed an animal feed composition of the invention can reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days and the like and/or any range therein.

In other aspects of the invention, a method of increasing the efficiency of feed utilization by an animal is provided, the method comprising feeding to said animal an animal feed composition of the invention in an amount effective to increase the efficiency of feed utilization by said animal as compared to a control animal that is not fed said animal feed composition.

Efficiency of feed utilization can be calculated as the gain in body weight of the animal per the amount of feed provided. In some embodiments, the body weight is the finished body weight prior to slaughter. In further embodiments, the feed provided is the amount of feed that is provided over a period of about 90 days to about 300 days. Thus, in some embodiments the feed provided is the amount of feed that is provided over a period of about 100 days to about 275 days, about 125 days to about 250 days, about 150 days to about 225 days, about 180 days to about 200 days, and the like.

Accordingly, in some embodiments, the time period (number of days) over which the weight gain is measured is 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 days, and the like, and/or any range therein.

In further aspects of the invention, the feeding value of corn by the animal is increased by about 1% to about 25% as compared to a control animal that is not fed said animal feed composition. The feeding value of corn equals the difference in feed efficiency of the feed composition of the present invention and the feed efficiency of a control animal that is not fed said feed composition, divided by the feed efficiency of said control animal that is not fed said feed composition, all of which is divided by the percent corn inclusion of said feed composition. Accordingly, in some embodiments, the increase in feeding value of corn can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, and the like, and/or any range therein. In particular embodiments, the increase in the feed value of corn is about 1% to about 10% as compared to a control. In a representative embodiment, the increase in the feed value is about 5% as compared to a control.

In further aspects of the invention, the efficiency of feed utilization by the animal is increased by about 0.005 to about 0.1 as compared to a control animal that is not fed said animal feed composition. Accordingly, in some embodiments, the increase in efficiency of feed utilization can be about 0.005, 0.006, 0.007, 0.008, 0.009, 0.01, 0.011, 0.012, 0.013, 0.014, 0.015, 0.016, 0.017, 0.018, 0.019, 0.02, 0.021, 0.022, 0.023, 0.024, 0.025, 0.026, 0.027, 0.028, 0.029, 0.03, and the like, and/or any range therein. In particular embodiments, the increase in the efficiency of feed utilization is about 0.005 to about 0.01 as compared to a control. In a representative embodiment, the increase in the efficiency of feed utilization is about 0.06 as compared to a control. The efficiency of feed utilization, also known as "G:F", is the average daily gain divided by the dry matter intake per day of the animal.

In some embodiments, the animal is fed about 1 lb to about 30 lbs of an animal feed composition of the invention per animal per day. Accordingly, in some embodiments, the animal is fed about 1 lb, 2 lbs, 3 lbs, 4 lbs, 5 lbs, 6 lbs, 7 lbs, 8 lbs, 9 lbs, 10 lbs, 11 lbs, 12 lbs, 13 lbs, 14 lbs, 15 lbs, 16 lbs, 17 lbs, 18 lbs, 19 lbs, 20 lbs, 21 lbs, 22 lbs, 23 lbs, 24 lbs, 25 lbs, 26 lbs, 27 lbs, 28 lbs, 29 lbs, 30 lbs of the animal feed composition of the invention per animal per day, and the like, and/or any range therein. In some embodiments, the animal is fed about 9 lbs to about 21 lbs of the animal feed composition of the invention per animal per day. In some embodiments, an animal can be fed the animal feed composition of the invention ad libitum, or about one time to about three times per day (e.g., 1, 2, 3) or any combination thereof.

The invention also contemplates a method of reducing liver abscesses in harvested (e.g., slaughtered) cattle, the method comprising the steps of: a) feeding an animal feed composition to cattle, wherein the animal feed composition comprises plant material from a transgenic plant or plant part (e.g., a transgenic corn plant or plant part) expressing a recombinant thermotolerant (optionally, microbial) α-amylase; and b) harvesting the cattle. The α-amylase of the invention is as described herein. In embodiments, the transgenic plant or plant part is a transgenic corn plant or plant part (e.g., steam flaked corn kernels), optionally comprising corn event 3272. In representative embodiments, the transgenic plant or plant part comprises about 1% to about 100% by weight of the plant material. The method can be practiced with any cattle, e.g., beef cattle (steers and/or heifers) and/or dairy cows. In embodiments, the cattle are feedlot cattle.

It is known in the art that the frequency of liver abscess formation increases with diets that are high in feed concentrates and low in forage (i.e., roughage). In representative embodiments, the method of reducing liver abscesses is practiced with cattle that are fed a high concentrate/low forage diet. In embodiments, the diet comprises forage in an amount less than or equal to about 20%, 15%, 14%, 13%, 12%, 11%, 10%, 9%, 8%, 7%, 6%, 5%, 4%, 3%, 2% or 1% (dry matter basis). In embodiments, the diet includes no or essentially no forage. In embodiments, the diet comprises at least about 80%, 85%, 86%, 87%, 88%, 89%, 90%, 91%, 92%, 93%, 94%, 95%, 96%, 97%, 98%, 99% or more feed concentrate (dry matter basis).

In embodiments, the overall frequency of liver abscess formation is reduced (e.g., by at least about 10%, 15%, 20%, 25%, 30%, 35%, 40%, 50%, 60% or more). In representative embodiments, the frequency of moderate and/or severe liver abscesses is reduced (e.g., by at least about 10%, 15%, 20%, 25%, 30%, 35%, 40%, 50%, 60% or more).

Also provided by the invention is a harvested (i.e., slaughtered) cattle carcass (or a plurality of harvested cattle carcasses) produced by a feeding method as described herein, wherein the harvested cattle carcass(es) comprises the liver of the harvested animal, and wherein there is a reduced incidence of liver abscesses in the liver of said harvested cattle carcass(es) as compared with carcasses from control cattle that are not fed plant material from a transgenic plant or plant part expressing a recombinant thermotolerant (e.g., microbial) α-amylase. In embodiments, the overall frequency of liver abscess formation is reduced (e.g., by at least about 10%, 15%, 20%, 25%, 30%, 35%, 40%, 50%, 60% or more). In representative embodiments, the frequency of moderate and/or severe liver abscesses is reduced (e.g., by at least about 10%, 15%, 20%, 25%, 30%, 35%, 40%, 50%, 60% or more).

The inventors have discovered that steam flaking plant material (e.g., corn kernels) expressing a recombinant thermotolerant (e.g., microbial) α-amylase (as described herein) has surprising and unexpected advantages as compared with a suitable control plant material that does not express a recombinant thermotolerant α-amylase. To illustrate, the inventors have found that the throughput rate of plant material (e.g., corn kernels) expressing the recombinant thermotolerant α-amylase can be increased as compared to plant material that does not express the α-amylase, e.g., under similar or even identical conditions (such as moisture, temperature and the like). In embodiments, the method results in a steam flaked product with substantially the same (for example, within about 5% or 10%) or even improved (reduced) flake thickness, substantially the same (for example, within about 5% or 10%) or even improved (reduced) geometric mean particle size and/or substantially the same (for example, within 5% or 10%) or improved (increased) flake density. An increased throughput rate has advantages as it may support the feeding of an increased number of animals and/or can translate into savings in terms of labor, water, energy (such as electricity and/or natural gas) and/or machinery costs.

Accordingly, the invention also provides methods of producing an animal feed by steam flaking a plant material comprising a recombinant thermotolerant (e.g., microbial) α-amylase. In representative embodiments, the method comprises: a) providing transgenic corn kernels (as described herein, e.g., whole shelled corn kernels) comprising a recombinant thermotolerant (e.g., microbial) α-amylase; and b) steam flaking the corn kernels to produce a steam flaked corn product; optionally, wherein the throughput rate is increased as compared with suitable control corn kernels that do not comprise a recombinant thermotolerant (e.g., microbial) α-amylase, e.g., under similar or even identical conditions (such as moisture, temperature and the like). In embodiments, the throughput rate is increased by at least about 10%, 15%, 20%, 25%, 30%, 35%, 40% or 50% or more. The "throughput" rate generally refers to the rate at which the plant material is processed through the entire steam flaking process and apparatus, which may optionally include a preliminary cleaning chamber/step, a preliminary soaking chamber/step, a follow on cooling chamber/step, a follow on drying chamber/step, and the like. In embodiments, the throughput rate refers specifically to the rate at which the plant material is processed through the steam chamber and flaking mill (e.g., rollers).

A "control" plant material, corn kernel and the like, as used herein, refers to a plant material or corn kernel that does not express a recombinant thermotolerant α-amylase (as described herein), e.g., the control plant material or corn kernel otherwise has similar properties to the transgenic plant material or corn kernels. A "control" steam flaked plant product or "control" steam flaked corn product, as used herein, is produced from a "control" plant material or corn kernel, respectively.

In representative embodiments, the transgenic corn kernels used in the steam flaking methods of the invention comprise corn event 3272.

In embodiments, the time to steam flake the transgenic plant material (e.g., corn kernels) expressing the recombinant thermotolerant (e.g., microbial) α-amylase can be reduced (e.g., by at least about 10%, 15%, 20%, 25%, 30%, 35%, 40%, 45%, 50% or more) as compared with the control plant material under otherwise similar conditions.

In representative embodiments, the digestability of starch in the steam flaked plant product (e.g., corn product) is increased (e.g., by at least about 1%, 2%, 3%, 4%, 5%, 6%, 7%, 8%, 9%, 10%, 12%, 15%, 20% or more) as compared with the digestability of starch in a control steam flaked corn product produced from the control corn kernels. Starch digestability is a measure of how much of the starch in the feed is converted to energy and used by the animal and can be determined by any method known in the art, including whole animal (e.g., fecal starch) and laboratory methods (e.g., as described in the accompanying Examples).

In embodiments, the steam flaked plant product (e.g., steam flaked corn product) produced by the steam flaking methods of the invention has a decrease in geometric mean particle size (e.g., at least about 1%, 2%, 3%, 4%, 5%, 6%, 7%, 8%, 9%, 10%, 12%, 15%, 20% or more) as compared with a control steam flaked plant product produced from a control plant product. Methods of determining geometric mean particle size are known in the art (see, e.g., the Examples).

In embodiments, the steam flaking methods of the invention may result in an increase in browning of the steam flaked plant product (e.g., corn kernels) prepared from plant material expressing a recombinant thermotolerant (e.g., microbial) α-amylase as compared with a control steam flaked plant product. In embodiments, the increase in browning in the steam-flaked product is observed during and/or after the cooling process. In embodiments, there is be an increase (e.g., by at least about 1%, 2%, 3%, 4%, 5%, 6%, 7%, 8%, 9%, 10%, 12%, 15%, 20%, 25%, 30%, 35%, 40%, 45%, 50% or more) in browning (e.g., non-enzymatic browning). Without being limited by any theory of the invention, it appears that the recombinant thermotolerant (e.g., microbial) α-amylase produces an increased concentration of soluble sugars, such as maltose and other reducing sugars, in the plant material. Reducing sugars can participate in the Maillard reaction (a chemical reaction between amino acids and reducing sugars producing a brown color), which may result in increased browning in steam flaked plant material (e.g., corn kernels) expressing a recombinant thermotolerant (e.g., microbial) α-amylase as compared with a control steam flaked plant product produced from a control plant material (e.g., as determined by visual inspection or by laboratory analysis).

The invention also provides a steam flaked plant product (e.g., corn product) produced by a steam flaking method as described herein. In embodiments, the steam flaked plant product can comprise one or more of the advantages discussed above (e.g., increased starch digestability, decreased geometric mean particle size, decreased flake thickness and/or increased flake density). In representative embodiments, the steam flaked plant product is utilized more efficiency when fed to animals (e.g., cattle) as compared with the utilization of a control steam flaked plant product. For example, the feed efficiency as measured by gain-to-feed ratio can be increased. Methods of determining an increase in feed efficiency and gain-to-feed ratio are described herein. For example, in embodiments, the gain-to-feed ratio is increased by at least about 1%, 2%, 3%, 4%, 5%, 6%, 7%, 8%, 9%, 10%, 12%, 15% or more as compared with a ration comprising a control steam flaked plant product. In representative embodiments, an increase in feed efficiency is observed when feeding the steam flaked plant product of the invention, even as compared with a control steam flaked plant product that has a substantially similar (e.g., within about 5% or 10%) level of starch availability. In embodiments, starch availability is in the range of equal to or greater than about 48%, 49%, 50% and/or equal to or less than about 51%, 52%, 53%, 54% or 55% (including any combination thereof, as long as the lower end of the range is less than the upper end of the range). In embodiments, starch availability is in the range of about 48% to 55%, about 48% to 54%, about 48% to 53%, about 48% to 52%, about 49% to 55%, about 49% to 54%, about 49% to 53%, about 49% to 52%, about 50% to 55%, about 50% to 54%, about 50% to 53%, about 50% to 52%, about 51% to 55%, about 51% to 54%, about 51% to 53% or about 51% to 52%.

Starch availability reflects how much of the starch is gelatinized (e.g., during the steam flaking process) and/or otherwise broken out of the protein matrix that typically encapsulates the starch granules (e.g., in the corn kernel), and is therefore available for enzymatic digestion (e.g., in the rumen). Starch availability can be measured by any method known in the art (e.g., Sindt et al., (2000) "Refractive Index: a rapid method for determination of starch availability in grains," *Kansas Agricultural Experiment Station Research Reports, Article* 398: Vol. 0: Iss. 1, found on the internet at doi.org/10.4148/2378-5977.1801). In steam flaking, starch availability is highly correlated with flake density, which is often used in practice as an indirect measure of starch availability.

The animal feed composition of the present invention can be fed to any animal, for example, a farm animal, a zoo animal, a laboratory animal and/or a companion animal. In some embodiments, the animal can be, but is not limited to, a bovine (e.g., domestic cattle (cows (e.g., dairy and/or beef)), bison, buffalo), an equine (e.g., horse, donkey, zebra, and the like), an avian (e.g., a chicken, a quail, a turkey, a duck, and the like; e.g., poultry), a sheep, a goat, an antelope, a pig (e.g., swine), a canine, a feline, a rodent (e.g., mouse, rat, guinea pig); a rabbit, a fish, and the like. In some embodiments, the animal can be a cow. In some embodiments the animal can be poultry. In other embodiments, the animal can be a chicken. In further embodiments, the animal can be swine. In still further embodiments, the animal can be a pig.

In further embodiments, the present invention provides a method for increasing the volume of milk produced by a dairy animal (e.g., a cow, a goat, and the like), comprising feeding to said dairy animal an animal feed composition of the present invention, wherein the volume of milk produced by said animal is increased by about 5% to about 200% as compared to the volume of milk produced by a control animal that is not provided said animal feed composition of the invention. In some embodiments, the increase in the volume of milk is in over a time period from about 1 to about 72 hours. In other embodiments, the volume of milk produced by said animal is increased by about 25% to about 175%, about 50% to about 150%, and the like. In further embodiments, the volume of milk produced by said animal is increased by about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195% and/or 200% as compared to a control animal that has not been fed the animal feed composition of the invention.

The terms "increase," "increasing," "increased," "enhance," "enhanced," "enhancing," and "enhancement" (and grammatical variations thereof), as used herein, describe an increase in the specified parameter, e.g., the average daily weight gain of an animal or the growth rate (weight gain) of an animal by feeding to said animal an animal feed composition of the invention, wherein the average daily weight gain or growth rate of the animal is increased by about 0.05 lbs/day to about 10 lbs/day or an increase in the efficiency of feed utilization by an animal by feeding to said animal the animal feed composition of the invention in an amount effective to increase the efficiency of feed utilization by said animal. This increase in the average daily weight gain, in the growth rate (weight gain), or in the efficiency of feed utilization by an animal can be observed by comparing the average daily weight gain, the growth rate (weight gain) or increase in the efficiency of feed utilization by the animal to an animal not fed an animal feed composition of the invention (i.e., a control).

As used herein, the terms "reduce," "reduced," "reducing," "reduction," "diminish," "suppress," and "decrease" (and grammatical variations thereof), describe, for example, a reduction of or decrease in the specified parameter, e.g., number and/or severity of liver abscess formation or the number of days needed to achieve a desired weight in an animal as compared to a control (e.g., a control animal that is not fed the animal feed composition).

The present invention is more particularly described in the following examples that are intended as illustrative only since numerous modifications and variations therein will be apparent to those skilled in the art.

EXAMPLES

Example 1—Effects of High-Amylase Feed Corn on Feedlot Performance and Carcass Quality of Finishing Beef Heifers Enogen® Feed Corn (EFC; Syngenta Seeds, LLC) is characterized by high-amylase expression in kernel endosperm. It was originally designed, and has been extensively used for the production of ethanol. Corn is well established as the most dominant ingredient fed to finishing cattle, as starch provides a majority of dietary energy. Ruminants have limited capacity for pancreatic-amylase secretion, and consequently are limited in post-ruminal digestion of starch (Harmon et al., 2004. *Can. J. Anim. Sci.* 84: 309). It is plausible that any ruminally undigested starch, could be further degraded in the small intestine by α-amylase produced by the grain. This would be an energetic advantage.

Many consider steam-flaking corn to be the optimal processing method to maximize energy utilized from the grain, and improvements by this processing technique are extensively documented (Owens et al., 1997. *J. Anim. Sci.* 75: 868; Zinn et al., 2002. *J. Anim. Sci.* 80: 1145). As far as the inventors are aware, the studies described herein are the first to evaluate steam-flaking EFC. Our results indicate that actions of EFC enhance the flaking process, resulting in greater throughput, possibly due to amylase increasing the rate of starch gelatinization.

Our objective in this study was to examine steam-flaking characteristics of EFC when fed to finishing beef heifers, and the effects on feedlot performance, carcass characteristics, and liver abscess prevalence and severity.

Materials and Methods

The Kansas State University Institutional Animal Care and Use Committee approved all protocols and procedures utilized in this study. The trial was initiated in December, and ended in April, taking place at the Kansas State University Beef Cattle Research Center, Manhattan, KS.

Experimental Design

A randomized complete block design with 2 treatments was carried out using 700 crossbred heifers (394 kg±8.5 initial BW). Two lots of cattle, blocked separately, were utilized in the trial. Three hundred fifty heifers received in June, were used previously in a receiving trial examining trace mineral supplementation. The second lot of cattle was received in November, targeting similar initial body weight (BW) between lots at study initiation. Heifers were blocked by lot, then BW, stratified, then randomly assigned to 1 of 28 dirt surfaced pens (25 animals/pen). Treatments randomly assigned within block, consisted of mill-run corn (CON) as control, steam-flaked to 360 g/L; and Enogen Feed Corn (EFC), steam-flaked to 390 g/L. Grain treatments were designed to target similar daily starch availability; based on preliminary work, a decision was made to flake EFC to a greater bulk density, and to flake with greater mill throughput to achieve this. Mill-run corn was flaked at approximately 6 tonne/h; EFC was flaked at approximately 9 tonne/h (50% increased mill throughput), decreasing steam-chest retention time.

Animal Processing, Housing, and Handling

Upon arrival at the Kansas State University Beef Cattle Research Center, heifers were given ad libitum access to alfalfa hay and water. Cattle were received on multiple dates for each lot, and were processed 24 to 48 hours after arrival. Processing of lot 1 included vaccination using a 5-way viral vaccine (Bovishield Gold-5; Zoetis, Parsippany, NJ), a 7-way clostridial (Ultrabac 7/Somubac; Zoetis), and an antibiotic (Micotil; Elanco Animal Health, Greenfield, Ind.) to target respiratory disease, as heifers from this lot were of younger age. Lot 2 vaccination was identical, except heifers from this lot were not treated with Micotil, and a topical parasiticide (Dectomax; Zoetis) was applied. During initial processing for both groups, animals were ear-tagged with a unique number for identification, and BW was recorded. On d 1 of trial initiation, starting BW was recorded as animals were sorted into pens, and received a trenbolone/estradiol implant (Component TE-IH with Tylan; Elanco Animal Health). On d 84 heifers were re-implanted (Component TE-200 with Tylan; Elanco Animal Health), and treated with a pour-on insecticide (Standguard; Elanco Animal Health).

Animals were housed in dirt surfaced pens that provided approximately 13 $m^2$ of surface area/animal; fences and gates were made of steel pipe, and divided in 2 by an additional electric fence. Automatic waterers allowing ad libitum access were shared between adjacent pens. Body weights were determined using a pen-scale and averaging pen-weight to determine mean BW for each pen.

Diet Preparation

Heifers were transitioned to finishing diets at the start of the trial over 21 d using 3 intermediate diets, with concentrate:roughage ratios of: 60:40, 71:29, and 92:8 (7 d/step) for gradual adaptation. Both grain types were steam-flaked daily, using a steam-flaker (R & R Machine Works; Dalhart, TX) with 46×91 cm corrugated rolls, and a steam chest able to hold approximately 4.25 tonnes corn. Grain characteristics allow mill-run corn in this system to be flaked at approximately 6 tonne/h without grain build-up on the rolls; EFC however could be flaked at maximum mill capacity without any grain build-up (~9 tonne/h). A system to apply moisture to grains prior to steaming (SarTec; Anoka, Minn.), allowed us to adjust grain conditioning so that grain dry matter (DM) was equivalent between treatments. Composition of experimental diets are shown in Table 1. Diets were re-formulated for final 39 days to include 300 mg/d Optaflexx (Elanco Animal Health). Cattle were fed ad libitum rations which were mixed and delivered once daily, beginning at approximately 0800 h. Feed intakes were visually monitored and adjusted daily as-needed, so that only trace amounts of residual feed were in bunks each morning. Orts were collected as-needed to account for unconsumed feed, and dried at 55 °C for 48 h for accurate adjustment of dry matter intake (DMI). Subsamples of each feed ingredient were collected weekly or upon arrival, dried at 55 °C for 48 h, and composited into monthly samples which were later analyzed for nutrient composition (SDK Labs; Hutchinson, KS).

TABLE 1

Composition of finishing diets fed to beef heifers[1]

| Item | Control | Enogen Feed Corn |
|---|---|---|
| Ingredient, % DM | | |
| Mill-run corn (steam-flaked) | 85.40 | 0.00 |
| Enogen Feed Corn (steam-flaked) | 0.00 | 85.40 |
| Ground alfalfa | 7.00 | 7.00 |
| Soybean meal | 1.64 | 1.64 |
| MGA[2] | 2.20 | 2.20 |
| Supplement[3] | 3.76 | 3.76 |
| Analyzed composition[4], % DM | | |
| CP[5] | 15.44 | 15.37 |
| ADF[6] | 6.51 | 7.15 |
| EE[7] | 3.58 | 4.16 |
| Ca | 0.60 | 0.59 |
| P | 0.23 | 0.24 |
| K | 0.64 | 0.68 |

[1]Optaflexx (Elanco Animal Health) was formulated into diet for final 39 days on feed, at a rate of 300 mg/d.
[2]Formulated to provide 1.76 mg/kg melengestrol acetate in total diet DM, blended with ground corn and 1% tallow as carrier.
[3]Contains urea, salt, limestone, trace mineral/vitamin premix, KCl to provide (on total diet DM basis) 0.15 mg/kg cobalt, 10 mg/kg copper, 0.50 mg/kg iodine, 20 mg/kg manganese, 0.10 mg/kg selenium, 30 mg/kg zinc, 2205 IU/kg vitamin A, 22 IU/kg vitamin E, and 36.4 mg/kg monensin (Rumensin, Elanco Animal Health).
[4]Analyzed nutrient composition of ingredients in total diet (SDK Labs).
[5]CP, crude protein
[6]ADF, acid detergent fiber
[7]EE, ether extract Harvest On d 136 all animals were weighed on a pen-scale immediately before shipping for slaughter. Final BW was calculated by multiplying the mean BW for each pen by 0.96 to account for 4% shrink during travel. Heifers were loaded onto trucks and transported approximately 440 km to a commercial abattoir in Lexington, Nebr. Records collected on the day of slaughter by trained Kansas State University personnel were: animal identification within kill-order, hot carcass weight (HCW), and liver abscess prevalence and severity using the Elanco scoring system (Liver Abscess Technical Information AI 6288; Elanco Animal Health). Liver scoring gives grades of: 0 (no abscess), or $A^-$, A, or $A^+$ for mild, moderate, and severe liver abscesses respectively. Following a chill period over 24 h, LM area, 12$^{th}$-rib subcutaneous fat, marbling score, USDA Yield Grade, and USDA Quality Grade data were collected. Dressing percentage was determined by averaging HCW within feedlot pen, and dividing that value by final shrunk BW.

Grain Characteristics

Daily observations on DM, starch availability, and particle size were measured for both grain types. Grain DM was determined by drying in a forced-air oven set to 105 °C for 24 h. If DM changes occurred, we would adjust the amount of moisture applied by the SarTec system accordingly to achieve equivalent moisture content between corn types. Starch availability was determined by steeping 25 g corn flakes in 100 ml 2.5%-amylogucosidase solution heated to 55 °C for 15 min (Sindt et al., 2006. *J. Anim. Sci.* 84: 424). The liquid fraction is then filtered, and percent soluble sugars are viewed on a handheld refractometer. Percent solubles and DM are then put into regression equations determining starch availability. Particle size was determined by weighing approximately 200 g of flaked-corn poured onto a set of sieves, with decreasing screen sizes in the order: 4750, 3350, 2360, 1700, 1180, 850, 600 μm, and a solid pan. The stack is placed into a Ro-Tap orbital shaker, with a rotary tapping cycle run for 5 min. Each individual sieve is cleaned, and particles weighed. Geometric particle size is calculated in a spreadsheet (Scott and Herrman, 2002. Evaluating Particle Size. Kansas State University Department of Grain Science and Industry. MF-2051, 1-6) using equations described by Pfost and Headley (Methods of determining and expressing particle size. In: H. Pfost (ed), Feed Manufacturing Technology II—Appendix C. Am. Feed Manufacturers Assoc. 1976:512-520).

Statistical Analyses

Analyses of BW, DMI, average daily gain (ADG), and feed efficiency used the MIXED procedure of the Statistical Analysis System (SAS version 9.4; SAS Inst. Inc., Cary, NC), with pen as the experimental unit, treatment as fixed effect, and block as a random effect. Categorical carcass traits (USDA Quality Grade, USDA Yield Grade, and liver abscess prevalence and severity) were analyzed with the GLIMMIX procedure of SAS, with the same parameters as above.

Results—

Four animals were removed from the CON group for non-treatment related reasons; 3 due to calving, and 1 was found deceased due to respiratory disease. Four animals were also removed from the EFC group for non-treatment reasons; 1 due to a bacterial infection, 1 due to respiratory disease, 1 due to a displaced abomasum, and 1 due to a hip-injury, all of which caused severe weight loss.

Grain Characteristics

Laboratory analysis (SDK labs) of nutrient composition between CON and EFC are shown in Table 2. Enogen Feed Corn had greater ADF ($P<0.01$), and potassium ($P=0.03$) components. Enogen Feed Corn also had a tendency ($P=0.06$) for greater fat content (ether extract [EE] as indicator). No differences between grains were evident between flaked grains for protein, calcium, or phosphorus.

TABLE 2

Nutrient analyses of mill-run and Enogen Feed Corn

| Item, % DM | CON | EFC | SEM | P-value |
|---|---|---|---|---|
| CP | 8.77 | 8.69 | 0.09 | 0.55 |
| ADF | 3.69 | 4.45 | 0.14 | <0.01 |

TABLE 2-continued

| Nutrient analyses of mill-run and Enogen Feed Corn | | | | |
|---|---|---|---|---|
| Item, % DM | CON | EFC | SEM | P-value |
| EE | 3.58 | 4.27 | 0.18 | 0.06 |
| Ca | 0.016 | 0.014 | 0.002 | 0.59 |
| P | 0.226 | 0.246 | 0.008 | 0.13 |
| K | 0.334 | 0.374 | 0.008 | 0.03 |

Characteristics of grains are presented in Table 3. By design, moisture content of both corn types had no difference after steam-flaking (P=0.55), and starch availability was similar, although there was a tendency (P=0.08) for EFC to yield a greater starch availability value. Even though EFC was flaked to a greater bulk density (390 vs 360 g/L), it still resulted in a smaller mean particle size (P<0.01).

TABLE 3

| Characteristics of flaked grains | | | | |
|---|---|---|---|---|
| Item | CON | EFC | SEM | P-value |
| DM, % | 78.8 | 78.9 | 0.70 | 0.55 |
| Starch availability, % | 51.3 | 52.1 | 0.30 | 0.08 |
| Geometric particle size, μm | 4405 | 4292 | 24 | <0.01 |

Feedlot Performance

Effects of EFC on gain and efficiency of feedlot heifers are found in Table 4. There was no difference in BW at trial initiation (P=0.52), but cattle fed EFC were heavier on the final day (P<0.01). Thus, over the 136-d period, the Enogen cattle had improved ADG (P<0.01). There was no difference in DMI between treatments (P=0.78), which results in 5% greater feed efficiency (Gain:Feed, G:F) for cattle fed EFC (P<0.01).

TABLE 4

| Feedlot performance of heifers finished using mill-run corn or EFC | | | | |
|---|---|---|---|---|
| Item | CON | EFC | SEM | P-value |
| Initial BW, kg | 395 | 394 | 8.6 | 0.52 |
| Final shrunk BW, kg | 588 | 599 | 10.7 | <0.01 |
| DMI, kg | 10.00 | 10.07 | 0.196 | 0.78 |
| ADG, kg | 1.60 | 1.69 | 0.028 | <0.01 |
| G:F | 0.160 | 0.168 | 0.002 | <0.01 |

Carcass Characteristics

Effects of EFC on carcass merit are displayed in Table 5. Improved daily gain in the feedlot for EFC fed cattle translated to carcass weight, as heifers produced approximately 6 kg heavier carcasses (P<0.01). No differences in longissimus muscle (LM) area or $12^{th}$ rib fat occurred. The CON diet yielded carcasses with a higher numerical marbling score (P=0.04), however, this did not result in an impact on USDA Quality Grades (P>0.33). There also was a tendency (P=0.09) for EFC fed heifers to result in more USDA Yield Grade 3 carcasses.

TABLE 5

| Carcass characteristics of beef heifers finished using mill-run corn or EFC | | | | |
|---|---|---|---|---|
| Item | CON | EFC | SEM | P-value |
| HCW, kg | 366 | 372 | 6.41 | <0.01 |
| LM area, $cm^2$ | 94.7 | 94.6 | 1.02 | 0.89 |
| $12^{th}$ rib fat thickness, cm | 1.16 | 1.19 | 0.045 | 0.21 |
| Marbling score† | 605 | 589 | 10 | 0.04 |
| USDA Prime, % | 6.6 | 4.9 | 1.68 | 0.33 |
| USDA Choice, % | 68.7 | 70.4 | 4.44 | 0.62 |
| USDA Select, % | 10.7 | 11.4 | 2.58 | 0.79 |
| USDA sub-Select, % | 9.0 | 9.3 | 2.61 | 0.68 |
| USDA Yield Grade | 2.07 | 2.15 | 0.069 | 0.13 |
| Yield Grade 1, % | 23.2 | 19.5 | 3.77 | 0.22 |
| Yield Grade 2, % | 49.4 | 47.7 | 3.01 | 0.64 |
| Yield Grade 3, % | 25.1 | 30.9 | 3.07 | 0.09 |
| Yield Grade 4, % | 2.0 | 2.0 | 0.76 | 1.00 |
| Yield Grade 5, % | 0.3 | 0.0 | 0.20 | 0.32 |

†500-599 = small degree of marbling; 600-699 = modest degree of marbling.

Liver abscess prevalence and severity are shown in Table 6. Note that no tylosin to prevent liver abscessation was included in experimental diets (Table 1). Finished beef heifers fed EFC had fewer total liver abscesses at slaughter than their CON counterparts (P=0.03). This difference occurs due to fewer moderate (P=0.03) and severe (P=0.11) liver abscesses in the EFC group. Detrimental effects of liver abscesses on cattle gain (Potter et al., 1985. *J. Anim. Sci.* 61: 1058) resulting in lighter, poorer quality carcasses (Brown and Lawrence, 2010. *J. Anim. Sci.* 88: 4037) have been well established. The relationship between liver abscess severity and HCW for each treatment is shown in FIG. 1. There were effects by diet (P<0.01), liver abscess severity (P<0.01), and tendency for a treatment x liver abscess interaction (P=0.09). The EFC group maintained heavier carcasses, and did not display the same decrease in HCW when abscess severity increased that was observed for CON cattle. While mode of action for the effect steam-flaked EFC had on liver abscessation is unclear at this time, the implications could be substantial, as new methods for the prevention of liver abscesses are needed as use of antibiotics is increasingly discouraged.

TABLE 6

| Liver abscess prevalence and severity in heifers fed mill-run corn or EFC | | | | |
|---|---|---|---|---|
| Item | CON | EFC | SEM | P-value |
| Total liver abscesses, % | 34.4 | 26.6 | 2.47 | 0.03 |
| Mild, % | 11.9 | 12.7 | 1.80 | 0.73 |
| Moderate, % | 14.7 | 9.2 | 1.74 | 0.03 |
| Severe, % | 7.5 | 4.6 | 1.40 | 0.11 |

More research will be needed with the EFC amylase expression trait to better understand modes of action to describe the enhanced animal performance we observed. At this stage it is unclear if the digestive advantage occurs ruminally or post-ruminally. We do believe high-amylase expression in EFC is likely the reason behind a more productive flaking process, where the starch gelatinizes more rapidly and is able to be flaked with much greater throughput, and decreased processing level (greater bulk density).

Implications

Enogen Feed Corn could be used advantageously by producers to reduce production costs associated with steam-flaking. Reduced steam use, reduced grain processing, increased mill throughput (50% in this study), and therefore reduced costs and labor are all benefits that occur prior to feed being delivered to bunks. Improvements in mill throughput, ADG, feed efficiency, HCW, and liver abscess mitigation, appear to be substantial benefits from the use of steam-flaked EFC.

Example 2—Digestion Characteristics of Amylase Corn Blends Undergoing Varying Moisture and Steam Treatments Followed by Flaking Treatment of Grains Mixtures of study grains were prepared using amylase whole shelled corn and a single source of mill-run, whole-shelled corn as a control. Amylase grain was blended with mill-run grain in proportions of 0:100, 25:75, 50:50, 75:25, and 100:0. Samples (1.8 kg) were placed into 3.8-L screw-top glass jars. Water was added at 0%, 3%, or 6% (w/w), jars were sealed, and subsequently placed horizontally onto a mechanical roller device, which slowly rotated jars to disperse water throughout the tempering period. Grain-filled jars remained on the roller for 1 hour, ensuring even mixing of grains and maximal exposure to moisture treatments. After 60 minutes, grain mixtures were removed from the jars and placed into perforated stainless steel baskets, which then were placed into a steam table equipped with 12 individual chambers. Samples were conditioned with steam for 15, 30, or 45 minutes, thus completing a 5×3×3 factorial treatment arrangement (5 grain mixtures, 3 moisture levels, and 3 conditioning times). Each of the 45 treatments was prepared in duplicate, making 90 total samples. Immediately after steam conditioning, samples were flaked using a dual-drive roller mill (R&R Machine), having the rolls set for a target density of 360 g/L (28 lb/bu). Samples were placed into the flaker through a conveyance system above the rolls, collecting the flaked product underneath rolls immediately thereafter. Bulk density was determined immediately using a Winchester cup, and the sample was then frozen for future particle size analysis. Starch availability was determined using an enzymatic assay shortly thereafter. Another portion of the grain was placed into a 105 °C forced-air oven for 24 hours for determination of moisture content. The remaining sample (roughly 700 g) was frozen and retained for future in vitro and in situ analysis.

Particle Size Analysis

Approximately 200 g of each grain was used for characterization of particle size distribution using a RoTap device equipped with a set of eight sieves and a bottom pan. Sieves were stacked, top to bottom, with progressively smaller screen sizes of 9.50, 6.70, 4.75, 3.35, 2.36, 1.70, and 1.18 mm, and placed over a pan for collection of fine particles. A flaked corn sample was added to the top sieve, and the stack was then placed onto the bed of a Ro-Tap orbital shaker for 5 minutes. Following agitation, the content of each screen was removed and weighed, and mean geometric diameter (Dgw) and standard deviation (Sgw) were calculated for each grain as described by Scott and Herrman. (Scott, B., T. Herrman. 2002. Evaluating Particle Size. Kansas State University Department of Grain Science and Industry. MF-2051, 1-6.).

Starch Availability

An enzymatic procedure by Sindt (Sindt, J. J. 2004. Factors influencing utilization of steam-flaked corn. Doctoral Dissertation, Kansas State University, Manhattan) was used for determination of starch availability for each sample. Amyloglucosidase (Sigma Chemical Company, St. Louis Mo.) in acetate buffer was prewarmed in a water bath to 55 C. Samples of flaked grain (25 g) were combined with 100 mL prewarmed buffer and incubated in a water bath for 15 min at 55 C. Following incubation, contents were strained through filter paper, and several drops of the particle-free filtrate were placed onto the prism of a hand-held refractometer. The refractive index provides a measure of water soluble components, and thus is a useful indicator of indicator of the extent of enzymatic hydrolysis. The resulting value (percent solubles) is expressed on a dry matter basis to yield estimates of starch availability.

In situ Dry Matter Disappearance

Approximately 2 g (dry matter basis) of each flaked sample were weighed and sealed into Dacron bags, prepared in triplicate. Measurements were taken over 3 days in the same week. The samples were assigned to 6 cannulated Jersey steers in blocks, thus accounting for animal effects on resulting disappearance values. Bags were suspended within rumina of fistulated steers for 14 hours, after which they were removed, thoroughly rinsed, and dried at 105 °C in a forced-air oven for 24 hours. Bags were then weighed, weight of the bag was subtracted, and dried residue was expressed as a percent of preincubation dry weight. Percent in situ dry matter disappearance (ISDMD) was calculated as:

$$100\times\frac{\text{dry sample weight}-\text{dry residue weight}}{\text{dry sample weight}}$$

In Vitro Gas Production and VFA Profiles

An in vitro procedure with ruminal fluid as inoculum was used to evaluate susceptibility of grains to digestion, with each sample prepared in duplicate (total of 180 observations). Two bottles without substrate (blanks) were used in each run to account for ruminal fluid contributions to volatile fatty acid (VFA) content of cultures. The Ankom RF Gas Production monitoring system (Ankom Technologies, Macedon, NY) was used to monitor fermentation profiles. Three grams of processed grain were placed into a 250-mL screw-top bottle, 10 mL of strained ruminal fluid and 140 mL McDougall's buffer were added, bottles were fitted with an Ankom radio frequency pressure-sensing module, cultures were placed into a shaking incubator at 39 C for 24 hours, and gas pressure within the bottles was recorded at 15-minute intervals throughout the incubation. After 24 hours, pH of the cultures was determined, and 4 mL of supernatant were combined with 1 mL of 25% metaphosphoric acid solution in scintillation vials, which were subsequently frozen for future use. Samples were later thawed, homogenized with a vortex mixer, supernatant was transferred to microcentrifuge tubes, contents were centrifuged at 15,000×g for 15 minutes, and the particulate-free supernatant was transferred to chromatography vials for measurement of VFA by gas chromatography. Volatile fatty acids were measured using an Aglient 7890 gas chromatograph (Aglient Technologies, Santa Clara, CA) equipped with a Nukol capillary column (15 m×0.35 mm, $d_f$ 0.50 μm), yielding concentrations of acetate, propionate, isobutyrate, butyrate, isovalerate, valerate, isocaproate, caproate, and heptanoate.

Statistical Analysis

The MIXED models procedure of the Statistical Analysis System (SAS version 9.4) was used to analyze data. Fixed effects included percent corn amylase, percent added moisture, steam conditioning time, and all 2- and 3-way interactions. Block was used as the random effect. Additional orthogonal contrasts allowed examination of linear and quadratic effects between treatments. Treatment effects were considered significant with a P-value less than 0.05.

There were no significant two or three way effects between treatments for any analysis.

Particle Size Analysis

Particle size plays a major role in the digestibility and fermentative properties of grains when fed to ruminants. There was a linear response (P<0.01) to percent inclusion of amylase corn in grain mixtures. The higher the percentage of amylase corn the lower the mean particle size. Moisture treatments had no effects on particle size (P>0.10). Steam conditioning time of the grains induced a quadratic effect (P<0.01), whereby 30 min of steam exposure resulted in the lowest mean particle size. This quadratic effect of steam mirrors that which is seen in subsequent assays.

Starch Availability

The starch availability assay is commonly used to characterize susceptibility of flaked grains to digestion. Pure amylase grain resulted in the greatest starch availability (52.7%), and starch availability declined linearly (P<0.01) in response to dilution of amylase corn with mill-run corn, suggesting that amylase within the amylase corn fraction of mixtures had relatively little impact on non-amylase corn, mill-run grain component of mixtures.

Starch availability increased linearly in response to increasing amounts of moisture (P<0.01). Steam conditioning time, on the other hand resulted in a quadratic effect (P<0.01), with the 30-min conditioning treatment yielding the greatest starch availability.

In situ Dry Matter Disappearance

Amylase corn content of grain mixtures had a notable impact (linear effect of amylase corn content; P<0.01) on in situ digestibility of the flaked grain mixtures. The absence of non-linear effects suggests that effects of amylase corn-derived amylase are essentially confined to the grain itself, and that there is no appreciable migration to non-amylase corn grains within the mixture.

In comparison to effects of amylase corn content, moisture addition during the tempering phase and steam conditioning time had relatively little impact on in situ dry matter disappearance of grains. There was a tendency for conditioning time to impact in situ dry matter disappearance in a quadratic manner (P=0.12); and the relationship is notably similar to that observed for starch availability, with 30 minutes of steam conditioning producing the greatest grain with the greatest is situ disappearance.

In Vitro Gas Production and VFA Profiles

Terminal substrate pH is a useful indicator of overall fermentative activity by the in vitro culture, with lower measurements indicating greater organic acid production, and therefore increased microbial digestion of grains. Terminal pH of cultures decreases in direct proportion to the amount of amylase corn grain incorporated into the mixtures (linear effect P<0.01). A significant quadratic effect (P<0.01) is observed for steam conditioning time, with 30-min yielding lowest culture pH. Moisture addition during the tempering phase had seemingly little effect on final pH of in vitro cultures.

As expected, changes in VFA production are consistent with differences in terminal pH of cultures. Samples were analyzed for caproate, isocaproate, and heptanoate; however, none of these minor VFAs were detected. Table 7 summarizes VFA profiles for flaked grains comprised of varying proportions of amylase corn and mill-run corn.

TABLE 7

Effect of Amylase corn content on VFA production by in vitro cultures of mixed ruminal microbes fed mixed steam-flaked grains as substrate.

| VFA, mmoles per | Amylase corn as % of total grain mixture | | | | | | P-values | | |
|---|---|---|---|---|---|---|---|---|---|
| gram of substrate DM | 0 | 25 | 50 | 75 | 100 | SEM | F-test | Linear | Quad |
| Acetate | 1.491 | 1.511 | 1.605 | 1.635 | 1.659 | 0.067 | <0.01 | <0.01 | 0.64 |
| Propionate | 1.692 | 1.727 | 1.845 | 1.901 | 1.953 | 0.067 | <0.01 | <0.01 | 0.83 |
| Butyrate | 0.528 | 0.486 | 0.521 | 0.516 | 0.543 | 0.067 | 0.06 | 0.20 | 0.06 |
| Isobutyrate | 0.004 | 0.000 | 0.003 | 0.003 | 0.002 | 0.002 | 0.03 | 0.98 | 0.33 |
| Valerate | 0.053 | 0.056 | 0.067 | 0.063 | 0.076 | 0.012 | <0.01 | <0.01 | 0.60 |
| Isovalerate | 0.008 | 0.005 | 0.007 | 0.005 | 0.004 | 0.002 | <0.01 | <0.01 | 0.78 |
| Total | 3.774 | 3.783 | 4.046 | 4.118 | 4.236 | 0.097 | <0.01 | <0.01 | 0.93 |

Production of VFA (acetate, propionate, valerate, isovalerate, and total VFA) increased linearly in response to increasing proportion of amylase corn grain (P<0.01). This indicates more extensive microbial digestion of amylase corn grain in comparison to the mill-run corn. The VFA contribute the vast majority of energy for maintenance and productive purposes in ruminants, and increased microbial digestion generally is consistent with increased total tract digestion of starch. Grains that are more susceptible to digestion by ruminal microbes are thus likely to greater total tract digestion, and thus may yield improvements in performance or efficiency. Increasing the proportion of amylase corn grain also decreased acetate:propionate ratio (P<0.01). This is a desirable effect, as downward shifts in acetate: propionate often are associated with decreases in methanogenesis, which is energetically more favorable.

In vitro gas production is a good indicator of total fermentative activity, with carbon dioxide and methane being the primary gaseous byproducts of ruminal fermentation. Statistical differences between treatments were analyzed in 6 hour intervals. At hour 6, the 0% amylase corn grain began to separate, being significantly lower than the 50, 75, and 100% treatments. At hour 12 amylase corn levels of 0% and 25% differed from all other treatments; 50% differed from 100%, while the difference between 75% and 100% was not significant. Hour 18 mirrored the treatment differences exactly to hour 12. At 24 hours of fermentation, the 50% amylase corn treatment closed the gap and could no longer be statistically distinguishable between 75% and 100%.

Amylase corn grain appears to be far more susceptible to digestion in comparison to the mill-run corn used as control, yielding substantial improvements in starch availability, in vitro and in situ digestion, and endproduct formation. Response to amylase corn grain in mixtures was in direct proportion to amylase corn content, suggesting that amylase corn-derived amylase has little or no impact on the other grain within mixtures. Amylase corn confers significant advantages for processing of grains by steam flaking.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

That which is claimed is:

1. A method of producing an animal feed, the method comprising:

a) providing transgenic corn kernels comprising corn event 3272 expressing a recombinant thermotolerant α-amylase; and b) steam flaking the transgenic corn kernels to produce a steam flaked transgenic corn product, wherein steam flaking the transgenic corn kernels comprises increasing the flake density by increasing the mill throughput rate by at least 20% as compared with the mill throughput rate for steam flaking control corn kernels that do not comprise the recombinant thermotolerant microbial α-amylase to produce a control steam flaked corn product, thereby decreasing steam-chest retention time, and wherein feeding the steam flaked transgenic corn product to an animal results in improved average daily gain and/or feed efficiency (gain:feed) as compared with feeding the control steam flaked corn product.

2. The method of claim 1, wherein the mill throughput rate is increased by at least 35% as compared with the mill throughput rate for steam flaking control corn kernels that do not comprise the recombinant thermotolerant microbial α-amylase.

3. The method of claim 1, wherein the time to steam flake the transgenic corn kernels is reduced by at least 20% as compared with the time to steam flake the control corn kernels.

4. The method of claim 1, wherein the digestability of starch in the steam flaked transgenic corn product is increased as compared with the digestability of starch in the control steam flaked corn product produced from the control corn kernels.

5. The method of claim 1, wherein the steam flaked transgenic corn product has a decrease in geometric mean particle size as compared with the control steam flaked corn product produced from the control corn kernels.

6. The method of claim 1, wherein in step (b) the transgenic corn kernels are steam-flaked at the same temperature as the control corn kernels are steam flaked.

* * * * *

SEQUENCE LISTING

```
Sequence total quantity: 5
SEQ ID NO: 1           moltype = AA  length = 436
FEATURE                Location/Qualifiers
REGION                 1..436
                       note = Synthetic
source                 1..436
                       mol_type = protein
                       organism = synthetic construct
SEQUENCE: 1
MAKYLELEEG GVIMQAFYWD VPSGGIWWDT IRQKIPEWYD AGISAIWIPP ASKGMSGGYS  60
MGYDPYDYFD LGEYYQKGTV ETRFGSKQEL INMINTAHAY GIKVIADIVI NHRAGGDLEW  120
NPFVGDYTWT DFSKVASGKY TANYLDFHPN ELHAGDSGTF GGYPDICHDK SWDQYWLWAS  180
QESYAAYLRS IGIDAWRFDY VKGYGAWVVK DWLNWWGGWA VGEYWDTNVD ALLNWAYSSG  240
AKVFDFPLYY KMDAAFDNKN IPALVEALKN GGTVVSRDPF KAVTFVANHD TDIIWNKYPA  300
YAFILTYEGQ PTIFYRDYEE WLNKDKLKNL IWIHDNLAGG STSIVYYDSD EMIFVRNGYG  360
SKPGLITYIN LGSSKVGRWV YVPKFAGACI HEYTGNLGGW VDKYVYSSGW VYLEAPAYDP  420
ANGQYGYSVW SYCGVG                                                 436

SEQ ID NO: 2           moltype = DNA  length = 1308
FEATURE                Location/Qualifiers
misc_feature           1..1308
                       note = Synthetic
source                 1..1308
                       mol_type = other DNA
                       organism = synthetic construct
SEQUENCE: 2
atggccaagt acctggagct ggaggagggc ggcgtgatca tgcaggcgtt ctactgggac  60
gtcccgagcg gaggcatctg gtgggacacc atccgccaga agatccccga gtggtacgac  120
gccggcatct ccgcgatctg gataccgcca gcttccaagg gcatgtccgg gggctactcg  180
atgggctacg acccgtacga ctacttcgac ctcggcgagt actaccagaa gggcacggtg  240
gagacgcgct tcgggtccaa gcaggagctc atcaacatga tcaacacggc gcacgcctac  300
ggcatcaagg tcatcgcgga catcgtgatc aaccacaggg ccggcggcga cctggagtgg  360
aacccgttcg tcggcgacta cacctggacg gacttctcca aggtcgcctc cggcaagtac  420
accgccaact acctcgactt ccaccccaac gagctgcacg cgggcgactc cggcacgttc  480
ggcggctacc cggacatctg ccacgacaag tcctgggacc agtactggct ctgggcctcg  540
caggagtcct acgcggccta cctgcgctcc atcggcatcg acgcgtggcg cttcgactac  600
gtcaagggct acggggcctg ggtggtcaag gactggctca actggtgggg cggctgggcg  660
gtgggcgagt actgggacac caacgtcgac gcgctgctca actgggccta ctcctccggc  720
gccaaggtgt tcgacttccc cctgtactac aagatggacg cggccttcga caacaagaac  780
atcccggcgc tcgtcgaggc cctgaagaac ggcggcacgg tggtctcccg cgacccgttc  840
aaggccgtga ccttcgtcgc caaccacgac acggacatca tctggaacaa gtacccggcg  900
tacgccttca tcctcaccta cgagggccag cccacgatct tctaccgcga ctacgaggag  960
tggctgaaca aggacaagct caagaacctg atctggattc acgacaacct cgcgggcggc  1020
tccactagta tcgtgtacta cgactccgac gagatgatct tcgtccgcaa cggctacggc  1080
tccaagcccg gcctgatcac gtacatcaac ctgggctcct ccaaggtggg ccgctgggtg  1140
tacgtcccga agttcgccgg cgcgtgcatc cacgagtaca ccggcaacct cggcggctgg  1200
gtggacaagt acgtgtactc ctccggctgg gtctacctgg aggccccggc ctacgacccc  1260
```

```
gccaacggcc agtacggcta ctccgtgtgg tcctactgcg gcgtcggc              1308

SEQ ID NO: 3           moltype = DNA  length = 2223
FEATURE                Location/Qualifiers
misc_feature           1..2223
                       note = Synthetic
source                 1..2223
                       mol_type = other DNA
                       organism = synthetic construct
SEQUENCE: 3
atggccaagt acctggagct ggaggagggc ggcgtgatca tgcaggcgtt ctactgggac  60
gtcccgagcg gaggcatctg gtgggacacc atccgccaga agatccccga gtggtacgac  120
gccggcatct ccgcgatctg gataccgcca gcttccaagg gcatgtccgg gggctactcg  180
atgggctacg acccgtacga ctacttcgac ctcggcgagt actaccagaa gggcacggtg  240
gagacgcgct tcgggtccaa gcaggagctc atcaacatga tcaacacggc gcacgcctac  300
ggcatcaagg tcatcgcgga catcgtgatc aaccacaggg ccggcggcga cctggagtgg  360
aacccgttcg tcggcgacta cacctggacg gacttctcca aggtcgcctc cggcaagtac  420
accgccaact acctcgactt ccaccccaac gagctgcacg cgggcgactc cggcacgttc  480
ggcggctacc cggacatctg ccacgacaag tcctgggacc agtactggct ctgggcctcg  540
caggagtcct acgcggccta cctgcgctcc atcggcatcg acgcgtggcg cttcgactac  600
gtcaagggct acggggcctg ggtggtcaag gactggctca actggtgggg cggctgggcg  660
gtgggcgagt actgggacac caacgtcgac gcgctgctca actgggccta ctcctccggc  720
gccaaggtgt tcgacttccc cctgtactac aagatggacg cggccttcga caacaagaac  780
atcccggcgc tcgtcgaggc cctgaagaac ggcggcacgg tggtctcccg cgacccgttc  840
aaggccgtga ccttcgtcgc caaccacgac acggacatca tctggaacaa gtacccggcg  900
tacgccttca tcctcaccta cgagggccag cccacgatct tctaccgcga ctacgaggag  960
tggctgaaca aggacaagct caagaacctg atctggattc acgacaacct cgcgggcggc  1020
tccactagta tcgtgtacta cgactccgac gagatgatct tcgtccgcaa cggctacggc  1080
tccaagcccg gcctgatcac gtacatcaac ctgggctcct ccaaggtggg ccgctgggtg  1140
tacgtcccga agttcgccgg cgcgtgcatc cacgagtaca ccggcaacct cggcggctgg  1200
gtggacaagt acgtgtactc ctccggctgg gtctacctgg aggccccggc ctacgacccc  1260
gccaacggcc agtacggcta ctccgtgtgg tcctactgcg gcgtcggcac atcgattgct  1320
ggcatcctcg aggccgacag ggtcctcacc gtcagcccct actacgccga ggagctcatc  1380
tccggcatcg ccaggggctg cgagctcgac aacatcatgc gcctcaccgg catcaccggc  1440
atcgtcaacg gcatggacgt cagcgagtgg gaccccagca gggacaagta catcgccgtg  1500
aagtacgacg tgtcgacggc cgtggaggcc aaggcgctga acaaggaggc gctgcaggcg  1560
gaggtcgggc tcccggtgga ccggaacatc ccgctggtgg cgttcatcgg caggctggaa  1620
gagcagaagg gccccgacgt catggcggcc gccatcccgc agctcatgga gatggtggag  1680
gacgtgcaga tcgttctgct gggcacgggc aagaagaagt tcgagcgcat gctcatgagc  1740
gccgaggaga agttcccagg caaggtgcgc gccgtggtca agttcaacgc ggcgctggcg  1800
caccacatca tggccggcgc cgacgtgctc gccgtcacca gccgcttcga gccctgcggc  1860
ctcatccagc tgcaggggat gcgatacgga acgccctgcg cctgcgcgtc caccggtgga  1920
ctcgtcgaca ccatcatcga aggcaagacc gggttccaca tgggccgcct cagcgtcgac  1980
tgcaacgtcg tggagccggc ggacgtcaag aaggtggcca ccaccttgca gcgcgccatc  2040
aaggtggtcg gcacgccggc gtacgaggag atggtgagga actgcatgat ccaggatctc  2100
tcctggaagg gccctgccaa gaactgggag aacgtgctgc tcagcctcgg ggtcgccggc  2160
ggcgagccag ggttgaagg cgaggagatc gcgccgctcg ccaaggagaa cgtggccgcg  2220
ccc                                                                2223

SEQ ID NO: 4           moltype = DNA  length = 3285
FEATURE                Location/Qualifiers
source                 1..3285
                       mol_type = other DNA
                       organism = synthetic construct
SEQUENCE: 4
gccaccccgg ccgactggcg ctcccagtcc atctacttcc tcctcaccga ccgcttcgcc  60
cgcaccgacg gctccaccac cgccacctgc aacaccgccg accagaagta ctgcggcggc  120
acctggcagg gcatcatcga caagctcgac tacatccagg gcatgggctt caccgccatc  180
tggatcaccc cggtgaccgc ccagctcccg cagaccaccg cctacggcga cgcctaccac  240
ggctactggc agcaggacat ctactccctc aacgagaact acggcaccgc cgacgacctc  300
aaggccctct cctccgccct ccacgagcgc ggcatgtacc tcatggtgga cgtggtggcc  360
aaccacatgg gctacgacgg cgccggctcc tccgtggact actccgtgtt caagccgttc  420
tcctcccagg actacttcca cccgttctgc ttcatccaga actacgagga ccagacccag  480
gtggaggact gctggctcgg cgacaacacc gtgtccctcc cggacctcga caccaccaag  540
gacgtggtga agaacgagtg gtacgactgg gtgggctccc tcgtgtccaa ctactccatc  600
gacggcctcc gcatcgacac cgtgaagcac gtgcagaagg acttctggcc gggctacaac  660
aaggccgccg gcgtgtactg catcggcgag gtgctcgacg tggacccggc ctacacctgc  720
ccgtaccaga acgtgatgga cggcgtgctc aactacccga tctactaccc gctcctcaac  780
gccttcaagt ccacctccgg ctcgatggac gacctctaca acatgatcaa caccgtgaag  840
tccgactgcc cggactccac cctcctcggc accttcgtgg agaaccacga caacccgcgc  900
ttcgcctcct acaccaacga catcgccctc gccaagaacg tggccgcctt catcatcctc  960
aacgacggca tcccgatcat ctacgccggc caggagcagc actacgccgg cggcaacgac  1020
ccggccaacc gcgaggccac ctggctctcc ggctacccga ccgactccga gctgtacaag  1080
ctcatcgcct ccgccaacgc catccgcaac tacgccatct ccaaggacac cggcttcgtg  1140
acctacaaga actggccgat ctacaaggac gacaccacca tcgccatgcg caagggcacc  1200
gacggctccc agatcgtgac catcctctcc aacaagggcg cctccggcga ctcctacacc  1260
ctctccctct ccggcgccgg ctacaccgcc ggccagcagc tcaccgaggt gatcggctgc  1320
accaccgtga ccgtgggctc cgacggcaac gtgccggtgc cgatggcggc cggcctcccg  1380
cgcgtgctct acccgaccga gaagctcgcc ggctccaaga tatgctcctc ctccaagccg  1440
```

-continued

```
gccaccctcg actcctggct ctccaacgag gccaccgtgg cccgcaccgc catcctcaac  1500
aacatcggcg ccgacggcgc ctgggtgtcc ggcgccgact ccggcatcgt ggtggcctcc  1560
ccgtccaccg acaacccgga ctacttctac acctggaccc gcgactccgg catcgtgctc  1620
aagaccctcg tggacctctt ccgcaacggc gacaccgacc tcctctccac catcgagcac  1680
tacatctcct cccaggccat catccagggc gtgtccaacc cgtccggcga cctctcctcc  1740
ggcggcctcg gcgagccgaa gttcaacgtg gacgagaccg cctacgccgg ctcctggggc  1800
cgcccgcagc gcgacggccc ggccctccgc gccaccgcca tgatcggctt cggccagtgg  1860
ctcctcgaca acggctacac ctccgccgcc accgagatcg tgtggccgct cgtgcgcaac  1920
gacctctcct acgtggccca gtactggaac cagaccggct acgacctctg ggaggaggtg  1980
aacggctcct ccttcttcac catcgccgtg cagcaccgcg ccctcgtgga gggctccgcc  2040
ttcgccaccg ccgtgggctc ctcctgctcc tggtgcgact cccaggcccc gcagatcctc  2100
tgctacctcc agtccttctg gaccggctcc tacatcctcg ccaacttcga ctcctcccgc  2160
tccggcaagg acaccaacac cctcctcggc tccatccaca ccttcgaccc ggaggccggc  2220
tgcgacgact ccaccttcca gccgtgctcc ccgcgcgccc tcgccaacca caaggaggtg  2280
gtggactcct tccgctccat ctacaccctc aacgacggcc tctccgactc cgaggccgtg  2340
gccgtgggcc gctacccgga ggactcctac tacaacggca acccgtggtt cctctgcacc  2400
ctcgccgccg ccgagcagct ctacgacgcc ctctaccagt gggacaagca gggctccctg  2460
gagatcaccg acgtgtccct cgacttcttc aaggccctct actccggcgc cgccaccggc  2520
acctactcct cctcctcctc cacctactcc tccatcgtgt ccgccgtgaa gaccttcgcc  2580
gacggcttcg tgtccatcgt ggagacccac gccgcctcca acggctccct ctccgagcag  2640
ttcgacaagt ccgacggcga cgagctgtcc gcccgcgacc tcacctggtc ctacgccgcc  2700
ctcctcaccg ccaacaaccg ccgcaactcc gtggtgccgc cgtcctgggg cgagacctcc  2760
gcctcctccg tgccgggcac ctgcgccgcc acctccgcct ccggcaccta ctcctccgtg  2820
accgtgacct cctggccgtc catcgtggcc accggcggca ccaccaccac cgccaccacc  2880
accggctccg gcggcgtgac ctccacctcc aagaccacca ccaccgcctc caagacctcc  2940
accaccacct cctccacctc ctgcaccacc ccgaccgccg tggccgtgac cttcgacctc  3000
accgccacca ccacctacgg cgagaacatc tacctcgtgg gctccatctc ccagctcggc  3060
gactgggaga cctccgacgg catcgccctc tccgccgaca agtacacctc ctccaacccg  3120
ccgtggtacg tgaccgtgac cctcccggcc ggcgagtcct tcgagtacaa gttcatccgc  3180
gtggagtccg acgactccgt ggagtgggag tccgacccga accgcgagta caccgtgccg  3240
caggcctgcg gcgagtccac cgccaccgtg accgacacct ggcgc                  3285

SEQ ID NO: 5           moltype = DNA  length = 1320
FEATURE                Location/Qualifiers
misc_feature           1..1320
                       note = Synthetic
source                 1..1320
                       mol_type = other DNA
                       organism = synthetic construct
SEQUENCE: 5
atggcgaagc acttggctgc catgtgctgg tgcagcctcc tagtgcttgt actgctctgc  60
ttgggctccc agctggccca atcccaggtc ctcttccagg ggttcaactg ggagtcgtgg  120
aagaagcaag gtgggtggta caactacctc ctggggcggg tggacgacat cgccgcgacg  180
ggggccacgc acgtctggct cccgcagccg tcgcactcgg tggcgccgca ggggtacatg  240
cccggccggc tctacgacct ggacgcgtcc aagtacggca cccacgcgga gctcaagtcg  300
ctcaccgcgg cgttccacgc caagggcgtc cagtgcgtcg ccgacgtcgt gatcaaccac  360
cgctgcgccg actacaagga cggccgcggc atctactgcg tcttcgaggg cggcacgccc  420
gacagccgcc tcgactgggg ccccgacatg atctgcagcg acgacacgca gtactccaac  480
gggcgcgggc accgcgacac gggggccgac ttcgccgccg cgcccgacat cgaccacctc  540
aacccgcgcg tgcagcagga gctctcggac tggctcaact ggctcaagtc cgacctcggc  600
ttcgacggct ggcgcctcga cttcgccaag ggctactccg ccgccgtcgc caaggtgtac  660
gtcgacagca ccgcccccac cttcgtcgtc gccgagatat ggagctccct ccactacgac  720
ggcaacggcg agccgtccag caaccaggac gccgacaggc aggagctggt caactgggcg  780
caggcggtgg gcggccccgc cgcggcgttc gacttcacca ccaagggcgt gctgcaggcg  840
gccgtccagg gcgagctgtg gcgcatgaag gacggcaacg gcaaggcgcc cgggatgatc  900
ggctggctgc cggagaaggc cgtcacgttc gtcgacaacc acgacaccgg ctccacgcag  960
aactcgtggc cattcccctc cgacaaggtc atgcagggct acgcctatat cctcacgcac  1020
ccaggaactc catgcatctt ctacgaccac gttttcgact ggaacctgaa gcaggagatc  1080
agcgcgctgt ctgcggtgag gtcaagaaac gggatccacc cggggagcga gctgaacatc  1140
ctcgccgccg acggggatct ctacgtcgcc aagattgacg acaaggtcat cgtgaagatc  1200
gggtcacggt acgacgtcgg gaacctgatc ccctcagact tccacgccgt tgcccctggc  1260
aacaactact gcgtttggga gaagcacggt ctgagagttc cagcggggcg gcaccactag  1320
```